(12) United States Patent
Juntunen et al.

(10) Patent No.: US 9,994,836 B2
(45) Date of Patent: Jun. 12, 2018

(54) FUNGAL ENDOGLUCANASE VARIANTS, THEIR PRODUCTION AND USE

(71) Applicant: AB Enzymes Oy, Rajamäki (FI)

(72) Inventors: Kari Juntunen, Rajamäki (FI); Marika Alapuranen, Rajamäki (FI); Leena Valtakari, Rajamäki (FI); Hanna-Mari Meriläinen, Rajamäki (FI); Terhi Puranen, Rajamäki (FI)

(73) Assignee: AB Enzymes Oy (FI)

(*) Notice: Subject to any disclaimer, the term of this patent is extended or adjusted under 35 U.S.C. 154(b) by 0 days. days.

(21) Appl. No.: 15/522,386

(22) PCT Filed: Oct. 23, 2015

(86) PCT No.: PCT/FI2015/050727
§ 371 (c)(1),
(2) Date: Apr. 27, 2017

(87) PCT Pub. No.: WO2016/066896
PCT Pub. Date: May 6, 2016

(65) Prior Publication Data
US 2017/0335303 A1 Nov. 23, 2017

(30) Foreign Application Priority Data
Oct. 27, 2014 (FI) ..................................... 20145941

(51) Int. Cl.
C12N 9/42 (2006.01)
C11D 3/386 (2006.01)
D06M 16/00 (2006.01)

(52) U.S. Cl.
CPC ........ *C12N 9/2437* (2013.01); *C11D 3/38645* (2013.01); *D06M 16/003* (2013.01)

(58) Field of Classification Search
CPC ....... C12N 9/2434; C12N 15/86; A61K 38/00
USPC ....................................................... 435/209
See application file for complete search history.

(56) References Cited

FOREIGN PATENT DOCUMENTS

| WO | 94/07998 A1 | 4/1994 |
|----|-------------|--------|
| WO | 2004/053039 A2 | 6/2004 |
| WO | 2007/071818 A1 | 6/2007 |
| WO | 2007071820 A1 | 6/2007 |
| WO | 2008151999 A1 | 12/2008 |
| WO | 2012106824 A1 | 8/2012 |

OTHER PUBLICATIONS

Koga J. et al., Purification and characterization of a new family 45 endoglucanase, STCE1, from Staphylotrichum coccosporum and its overproduction in Humicola insolens. Applied and Enviornmental Microbiology, Jul. 2008, vol. 14, No. 13, p. 4210-4217.
Qin Y. et al. Engineering endoglucanase II from Trichoderma reesei to improve the catalytic efficiency at a higher pH optimum. Journal of Biotechnology, 2008. vol. 135, No. 2, p. 190-195.
Bailey, M.J. et al, Induction, Isolation and Testing of Stable Trichoderma reesi Mutants with Improved Production of Solubilizing Cellulase, Enzyme Microb. Technol., 1981, vol. 3, pp. 153-157.
Coen, D.M., The Polymerase Chain Reaction, Current Protocols in Molecular Biology, 2006, 15.0.1-15.0.3.
Gellissen, G. (Ed.), 2005, Production of Recombinant Proteins. Novel Microbial and Eucaryotic Expression Systems, , Weinham: WILEY-VCH Verlag GmbH & KGaA.
Haakana, H. et al, Cloning of Cellulase Genes from Melanocarpus albomyces and Their Efficient Expression in Trichoderma Reesi, Enzyme and Microbial Technology, 2004, vol. 34, pp. 159-167.
Henrissat, B., A Classification of Glycosyl Hydrolases Based on Amino Acid Sequence Similarities, Biochem. J., 1991, vol. 280, pp. 309-316.
Henrissat, B. et al, Updating the Sequence-Based Classification of Glycosyl Hydrolases, Biochem. J., 1996, vol. 316, pp. 695-696.
Joutsjoki, V.V. et al, Transformation of Trichoderma reesi with the Hormoconis resinae glucoamylase P (gamP) Gene: Production of a Heterologous Glycoamylase by Trichoderma reesi, Current Genetics, 1993, vol. 24, pp. 223-228.
Karhunen T. et al, High Frequency One-Step Gene Replacement in Trichoderma reesi. I. Endoglucanase I overproduction, Mol Gen Genet, 1991, vol. 241, pp. 515-522.
Paloheimo, M. et al, High-Yield Production of a Bacterial Xylanase in the Filamentous Fungus *Trichoderma reesei* Requires a Carrier Polypeptide with an Intact Domain Structure, Applied and Environmental Microbiology, Dec. 2003, vol. 69, No. 12, pp. 7073-7082.
Penttila, M. et al, A Versatile Transformation System for the Cellulolytic Filamentous Fungus *Trichoderma reesei*, Gene, 1987, vol. 61, pp. 155-164.
Sambrook, J. and Russell, D.W. (2001) Plasmids and Their Usefulness in Molecular Cloning, Molecular Cloning a Laboratory Manual (3rd ed.), pp. 1.31-1.42, 1.62-1.64, Cold Spring Harbor, NY: Cold Spring Harbor Laboratory Press.
Sambrook, J. and Russell, D.W. (2001) Plasmids and Their Usefulness in Molecular Cloning, Molecular Cloning a Laboratory Manual (3rd ed.), pp. 1.84-1.87, Cold Spring Harbor, NY: Cold Spring Harbor Laboratory Press.
Sambrook, J. and Russell, D.W. (2001) Plasmids and Their Usefulness in Molecular Cloning, Molecular Cloning a Laboratory Manual (3rd ed.), pp. 1.105-1.111, Cold Spring Harbor, NY: Cold Spring Harbor Laboratory Press.
Sambrook, J. and Russell, D.W. (2001) Gel Electrophoresis of DNA and Pulsed-field Agarose Gel Electrophoresis, Molecular Cloning a Laboratory Manual (3rd ed.), pp. 5.29-5.35, Cold Spring Harbor, NY: Cold Spring Harbor Laboratory Press.
Sambrook, J. and Russell, D.W. (2001) Gel Electrophoresis of DNA and Pulsed-field Agarose Gel Electrophoresis, Molecular Cloning a Laboratory Manual (3rd ed.), pp. 5.4-5.17, Cold Spring Harbor, NY: Cold Spring Harbor Laboratory Press.
Smith, T.F. et al, Identification of Common Molecular Subsequences, J. Mol. Biol., 1981, vol. 147, pp. 195-197.

*Primary Examiner* — Tekchand Saidha
(74) *Attorney, Agent, or Firm* — Banner & Witcoff, Ltd.

(57) ABSTRACT

The invention relates to novel variants of fungal endoglucanases, their production and means for their production. Especially the invention relates to variants of *Acremonium thermophilum* Cel45A. The invention further relates to enzyme preparations and detergent compositions comprising at least one novel variant endoglucanase as well as to processes for treating cellulosic material therewith. The novel variant endoglucanase polypeptides have improved performance in textile applications, especially in biofinishing and biostoning, and in detergent applications, in fabric care and color maintenance, especially in prevention and removal of fuzz and pills, in color care and revival.

21 Claims, 5 Drawing Sheets

FUNGAL ENDOGLUCANASE VARIANTS, THEIR PRODUCTION AND USE

RELATED APPLICATION DATA

This application is a National Stage Application under 35 U.S.C. 371 of co-pending PCT application number PCT/FI2015/050727 designating the United States and filed Oct. 23, 2015; which claims the benefit of FI application number 20145941 and filed Oct. 27, 2014 each of which are hereby incorporated by reference in their entireties.

FIELD OF THE INVENTION

The invention relates to novel variants of fungal endoglucanases, their production and means for their production. The invention further relates to enzyme preparations comprising at least one of the novel endoglucanase variants as well as to processes for treating cellulosic material therewith. The novel endoglucanase variants are especially useful in textile treatment and detergent applications.

BACKGROUND OF THE INVENTION

Cellulose is a linear polysaccharide of glucose residues connected by β-1,4 linkages. It is the main component of plant cell walls, and the basic building block for many textiles and for paper. It gives plant cells remarkable strength helping them to resist mechanical stress and osmotic pressure. Cotton is the purest natural form of cellulose.

Cellulases or cellulolytic enzymes are a group of glycoside hydrolase enzymes that catalyze the hydrolysis of beta-1,4 glycosidic linkages in the cellulose polymer. Cellulases are known to be produced by a large number of bacteria, yeast, and fungi. Cellulases comprise a catalytic domain/core (CD) expressing cellulase activity. In addition to the catalytic domain, the cellulase molecule may comprise one or more cellulose binding domains (CBDs), also named as carbohydrate binding domains/modules (CBD/CBM). The CBD enhances the binding of the enzyme to a cellulose-containing fiber and increases the efficacy of the catalytic domain.

Cellulases are utilized, based on their properties, in various industrial fields. In the textile industry, cellulases are used in denim finishing for creating a fashionable stone washed appearance in denim cloths in a biostoning process, and they are also used, for instance, to clean fuzz and prevent formation of pills on the surface of cotton garments. In detergent industry, cellulases are used to brighten colors, to prevent graying and pilling of garments and to improve cleaning. Cellulases are further used in food industry, including baking, and animal feed manufacturing, and they have a great potential in the pulp and paper industry, for instance, in deinking to release ink from fiber surfaces, in improving pulp drainage and fiber modification, in energy reduction, in refining and drying stages of paper, board and pulp production. Cellulases are also utilized in hydrolysis of lignocellulosic material for, e.g. bioethanol production.

The practical use of cellulases is hampered by the nature of the cellulase compositions, which often are enzyme mixtures having a variety of activities and substrate specificities. The unique properties of each cellulase make some more suitable for certain purposes than others. The wide spectrum of industrial uses for cellulases has established a need for commercial cellulase products containing different cellulase components and functioning in different pH and temperature ranges. The production costs of microbiologically produced enzymes are tightly connected with the productivity of the enzyme producing strain and the final activity yield in the fermentation broth. There exists a need in the art to identify enzyme variants and enzymatic compositions that have improved efficacy and capacity to act on a greater variety of cellulosic materials.

US2011250674 (A1) provides a method for improving the properties of a cellulolytic enzyme i.e., an endo-1,4-glucanase, by amino acid substitution, deletion or insertion. The invention discloses *Humicola insolens* cellulase variants, which have been improved with respect to activity; and/or sensitivity to anionic tensides; and/or pH optimum and pH profile as well as stability. US20130244292 relates to a family 5 glycoside hydrolase variant having endoglucanase activity and to polynucleotides encoding the polypeptides.

Although cellulolytic enzymes have been used successfully in commercial applications for many years, a need still exists for new cellulolytic enzymes with altered properties, such as improved performance, in varying industrial applications.

BRIEF DESCRIPTION OF THE INVENTION

An object of the present invention is thus to provide novel variants of cellulolytic enzymes, which show improved performance, when compared to the parental enzyme.

The objects of the invention are achieved by a variant endoglucanase polypeptide comprising an amino acid sequence having at least 95% sequence identity with amino acids 1 to 214 of SEQ ID NO: 1 and an amino acid substitution at one or more positions selected from the group consisting of 51, 75, 77, 82, 109, 116, 118, 135, 150 and 205, the positions being numbered with reference to SEQ ID NO: 1, wherein the variant polypeptide has endoglucanase activity.

The invention is further directed to an isolated polynucleotide selected from the group consisting of:

a) a polynucleotide or complementary DNA encoding an endoglucanase polypeptide variant of claim 1;

b) a polynucleotide or complementary DNA encoding an endoglucanase polypeptide variant of claim 8;

c) a polynucleotide encoding a fragment of a polypeptide encoded by a polynucleotide of a) or b) wherein said fragment is having endoglucanase activity;

d) a polynucleotide comprising a nucleotide sequence which is degenerate to the nucleotide sequence of a polynucleotide sequence of a), b) or c); or the complementary strand of such a polynucleotide.

The invention is still further directed to an expression vector comprising said polynucleotide and a host cell comprising said expression vector.

Still further the invention is directed to a method for the production of the endoglucanase polypeptide variant, comprising the steps of transforming a host cell with an expression vector encoding said polypeptide, and culturing said host cell under conditions enabling expression of said polypeptide, and optionally recovering and purifying said polypeptide.

The invention is further directed to an enzyme preparation comprising at least one novel endoglucanase polypeptide variant of the invention and the use of said enzyme preparation especially in textile and detergent industry, but also in biomass processing, preferably in biofuel, starch, pulp and paper, food, baking, feed or beverage industries.

In one aspect, the present invention relates to a detergent composition comprising an endoglucanase polypeptide variant or an enzyme preparation of the invention and optionally auxiliaries, such as surface active agents, surfactants, bleaching agents, builders, stabilizers, buffers, mediators of an oxidase, anti-corrosion agents, polymers/antiredeposition agents, optical brighteners, dyes, pigments, caustics, abrasives and preservatives, perfumes, etc.

The invention also relates a process for treating cellulosic material, wherein said process comprises contacting the cellulosic material with the endoglucanase polypeptide variant or enzyme preparation of the invention. The treating of cellulosic material involves detergent applications, biostoning or biofinishing.

Specific embodiments of the invention are set forth in the dependent claims. Other objects, details and advantages of the present invention will become apparent from the following drawings, detailed description and examples. It should be understood, however, that the embodiments given in the description, drawings and in the examples are for illustrative purposes only, and that various changes and modifications are possible within the scope of the claims.

The present invention describes improved, higher performance cellulases for use in various industrial processes. The invention discloses a number of amino acid residue positions important for the properties of an endoglucanase enzyme and thereby for the performance thereof. Particularly, the present invention discloses variant endoglucanase polypeptides having improved performance in textile applications, especially in biofinishing and biostoning, and in detergent applications, in fiber care and color maintenance, especially in prevention and removal of fuzz and pills, in color care and revival. The variant endoglucanases of the invention perform well at broad pH range and notably at neutral and alkaline pH. This enables biofinishing treatment simultaneously with dyeing, leading to considerable cost savings. The color fastness is often better at neutral conditions. These novel endoglucanases are also effective at smaller enzyme dosages than the reference enzymes.

BRIEF DESCRIPTION OF THE DRAWINGS

In the following the invention will be described in greater detail by means of preferred embodiments with reference to the attached drawings, in which

FIG. 2 shows the performance of *A. thermophilum* ACM0 variants in detergent application as an increase of darkness (sum of −ΔL*of 4 stripes) after 10 washing and tumbling cycles of test monitors. Commercial preparation Carezyme® and ACM0 cellulase were used for comparison. Washing conditions in Launder-Ometer were: 40° C., 60 min, 16° dH, commercial liquid detergent 5 g/l, pH approx. 8.5, enzyme dosage 0.2 mg AEP/l;

FIG. 3 shows the performance of *A. thermophilum* ACM0 variants ACM72 and ACM88 in detergent application as an increase of darkness (sum of −ΔL*of 4 stripes) after 10 washing and tumbling cycles of test monitors. Commercial preparation Carezyme® and the ACM0 cellulase were used for comparison. Washing conditions in Launder-Ometer were: 40° C., 60 min, 16° dH, commercial liquid detergent 5 g/l, pH approx. 8.5, enzyme dosage 0.1 mg AEP/l;

FIG. 5 shows the performance of *A. thermophilum* Cel45A cellulase variants ACM90 and ACM91 in detergent application as an increase of darkness (sum of −ΔL*of 4 stripes) after 10 washing and tumbling cycles of test monitors. At_Cel45A cellulase was used for comparison. Washing conditions in Launder-Ometer were: 40° C., 60 min, 16° dH, commercial liquid detergent 5 g/l, pH approx. 8.5, enzyme dosage 0-0.2 or 0-0.4 mg AEP/l;

DETAILED DESCRIPTION OF THE INVENTION

Figure 1:
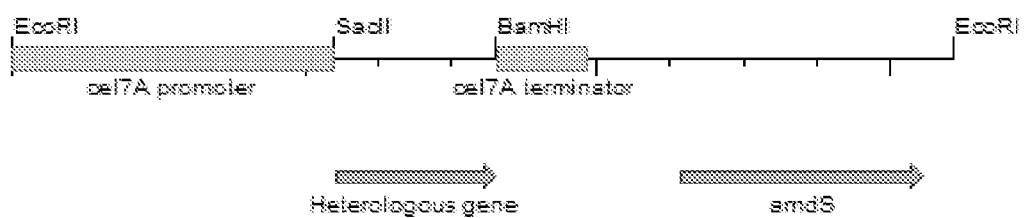
FIG. 1 illustrates a schematic picture of the expression cassettes used in the transformation of *Trichoderma reesei* A152 for production of *Acremonium thermophilum* cellulases of the invention. The recombinant genes were under control of *T. reesei* cel7A promoter and transcription termination was ensured with the addition of the *T. reesei* cel7A terminator. The amdS gene (amdS) was included for selection of the transformants.

Cellulolytic enzymes or cellulases are enzymes having cellulolytic activity, which means that they are capable of hydrolysing cellulosic substrates or derivatives thereof into smaller saccharides. Cellulolytic enzymes thus include both cellulases and hemicellulases. Cellulases include (1) endoglucanases (EG, EC 3.2.1.4) which cut internal beta-1,4-glucosidic bonds; (2) exoglucanases or cellobiohydrolases (CBH, EC 3.2.1.176, EC 3.2.1.91) that cut the dissaccharide cellobiose from the reducing or non-reducing end of the crystalline cellulose polymer chain and (3) beta-1,4-glucosidases (BG, EC 3.2.1.21) which hydrolyze the cellobiose and other short cello-oligosaccharides to glucose.

The present invention relates in particular to endoglucanases. Specifically, the present invention relates to fungal endoglucanases belonging to glycosyl hydrolase family 45, especially to variants of these endoglucanases. More specifically the invention relates to variants of *Acremonium thermophilum* Cel45A endoglucanase polypeptide. "Glycosyl hydrolase family 45" refers to the glycosyl hydrolase family as defined by Henrissat 1991, and Henrissat and Bairoch 1993, 1996.

The variants of the invention were designed by protein engineering techniques on the basis of amino acid sequence comparison between the catalytic core domains of *Acremonium thermophilum* Cel45A and *Geomyces pannorum* Cel45A (SEQ ID NO:1 and SEQ ID NO:2, respectively) and their three-dimensional structures. The amino acid and nucleotide sequences of Acremonium *thermophilum* Cel45A and *Geomyces pannorum* Cel45A and their isolation are disclosed in patent applications FI20055692 and FI20086253 (AB Enzymes Oy, FI).

The invention relates to a variant endoglucanase polypeptide or an enzymatically active fragment of it, comprising an amino acid sequence having at least 95% sequence identity with amino acids 1 to 214 of SEQ ID NO: 1 and an amino acid substitution at one or more positions selected from the group consisting of 51, 75, 77, 82, 109, 116, 118, 135, 150 and 205, the positions being numbered with reference to SEQ ID NO: 1, wherein the variant polypeptide has endoglucanase activity. Especially, the variant endoglucanase polypeptide has at least 96, 97, 98 or 99% identity with amino acids 1 to 214 of SEQ ID NO: 1.

The variant endoglucanase polypeptide may contain any combination of said substitutions.

By the term "identity" is here meant the identity between two amino acid sequences. The degree of identity is determined by using EMBOSS Water pairwise sequence alignment program at EBI (European Bioinformatics Institute) http://www.ebi.ac.uk/Tools/psa/emboss_water/ with the following parameters: BLOSUM62, Gap open 10, Gap extend 0.5. The algorithm is described in Smith and Waterman (1981).

In one embodiment of the invention the polypeptide variant comprises a substitution at a position corresponding to one or more of S51N, A75S, A77S, S82Q, S109N, S116Q, S116E, Q118H, A135Q, S150Q and S205N.

In another embodiment the polypeptide variant has a substitution at the positions corresponding to S51N, S82Q, S109N, S116E, Q118H, A135Q, S150Q and S205N.

Still in another embodiment the polypeptide variant has a substitution at the positions corresponding to S51N, S82Q, S116E, Q118H, A135Q, S150Q and S205N.

According to one embodiment the variant endoglucanase polypeptide has an amino acid sequence of SEQ ID NO: 12 or 13 and an amino acid substitution at one or more positions selected from the group consisting of 51, 75, 77, 82, 109, 116, 118, 135, 150 and 205, the positions being numbered with reference to SEQ ID NO: 1.

According to one embodiment the variant endoglucanase polypeptide has an amino acid sequence of SEQ ID NO: 12 and a substitution at the positions corresponding to S51N, S82Q, S109N, S116E, Q118H, A135Q, S150Q and S205N.

According to another embodiment the variant endoglucanase polypeptide has an amino acid sequence of SEQ ID NO: 12 and a substitution at the positions corresponding to S51N, S82Q, S116E, Q118H, A135Q, S150Q and S205N.

According to one embodiment the variant endoglucanase polypeptide has an amino acid sequence of SEQ ID NO: 13 and a substitution at the positions corresponding to S51N, S82Q, S109N, S116E, Q118H, A135Q, S150Q and S205N.

According to another embodiment the variant endoglucanase polypeptide has an amino acid sequence of SEQ ID NO: 13 and a substitution at the positions corresponding to S51N, S82Q, S116E, Q118H, A135Q, S150Q and S205N.

In the present invention the polypeptide variants are derived from a parental molecule cel45A-ACM0 (SEQ ID NO: 3), which is a polynucleotide containing a region encoding for the catalytic core domain of *A. thermophilum* Cel45A attached to the linker and CBM region of *T. reesei* Cel7A, or from a parental molecule cel45A (SEQ ID NO: 9), which is a polynucleotide containing a region encoding for the catalytic core domain of *A. thermophilum* Cel45A endoglucanase and having the natural linker and CBM region. However, any polynucleotide sequence encoding for the catalytic core domain of *A. thermophilum* Cel45A may be used for creating the polypeptide variants of the invention.

As used herein, a "variant" is a polypeptide having an amino acid substitution, deletion or insertion at one or more positions. Preferably the variants have a substitution. The variants are generated by mutagenesis i.e. by deliberately introducing changes in DNA to produce mutant gene products i.e. proteins. The changes or modifications of the parental nucleotide sequence may be introduced by several methods including e.g. site-directed and random mutagenesis. For site-directed mutagenesis a protein structure and good understanding of the structure-function relationship is beneficial. In the absence of such deep understanding, methods based on random mutagenesis may be used.

A variant may be obtained e.g. by altering hydrogen bond contacts, altering charge distribution, introduction of a salt bridge, introduction of metal binding sites, filling an internal structural cavity with one or more amino acids with bulkier side groups (in e.g. regions which are structurally mobile), substitution of histidine residues with other amino acids, removal of a deamination site, or by helix capping. Stability of the protein may be improved by substitution of at least one amino acid with cysteine residue or insertion of one or more cysteine residues which creates at least one disulfide bridge.

The endoglucanase polypeptide variants of the invention are preferably recombinantly produced fusion proteins. They are conveniently prepared using the generally known recombinant DNA technology. Briefly, the polynucleotide encoding the endoglucanase is cloned and inserted into an expression vector, transformed into a host cell and expressed. Methods for protein production by recombinant technology in different host systems are well known in the art (Sambrook and Russel, 2001; Coen, 2001; Gellissen, 2005). Preferably, the polypeptide variants are produced as extracellular proteins that are secreted into the culture medium, from which they can easily be recovered and isolated.

The endoglucanase polypeptide variants may comprise in addition to the catalytic core domain, which forms the active or functional site of the enzyme, one or more "cellulose binding domains" ("CBDs"), also named as carbohydrate binding domains/modules (CBD/CBM) located either at the N- or C-terminus of the catalytic domain. CBMs have carbohydrate-binding activity and they mediate the binding of cellulase to crystalline cellulose but have little or no effect on hydrolytic activity of the enzyme on soluble substrates. The endoglucanase variants of the invention may optionally also contain a signal sequence and a linker connecting the CBM and catalytic domain via a flexible and highly glycosylated region. The modular structure of cellulases containing carbohydrate binding module and/or the linker region is well known in the art. The carbohydrate binding module and the linker region may be heterologous or homologous. "Heterologous" as used in the present context means that the CBM and/or the possible linker part of the variant endoglucanase polypeptide are obtained from a different organism than the cellulolytically active core domain. "Homologous" as used herein means that the CBM and/or the possible linker part of the variant are from the same organism as the cellulolytically active core. The invention discloses that any linker or CBM may be used in the variant endoglucanase polypeptide. The performance of the endoglucanase polypeptide variants of the invention is improved as compared to the parental enzyme regardless of the origin of the linker or CBM region (Examples 3 and 6).

"Enzymatically active fragment" refers to the part of a specific amino acid sequence that is long enough to have the desired enzymatic activity. In other words a fragment may be e.g. only the mature part of the polypeptide or even a subsequence of the mature part. It may or may not contain a linker and CBM domain. The enzymatic activity refers herein to cellulolytic activity meaning catalytic ability of the polypeptide to hydrolyse cellulose or derivatives thereof. The enzymatic activity may be determined as described in Example 1.

The present invention relates further to novel polynucleotides which comprise nucleotide sequences having SEQ ID NO: 4 to 8 (Table 1), or fragments thereof long enough to encode an enzymatically active endoglucanase variants, or a sequence encoding a novel polypeptide variant as defined above, including complementary strands thereof. The polynucleotides of the invention are recombinant molecules containing genetically engineered non-naturally occurring sequences. "Polynucleotide" as used herein refers to both RNA and DNA, and it may be single stranded or double stranded. It may also be complementary DNA (cDNA). With cDNA is meant a DNA molecule synthesized from a messenger RNA template obtained from a eukaryotic or prokaryotic organism. Further, the polynucleotide may be degenerate as a result of the genetic code to any one of the sequences as defined above. This means that different codons may code for the same amino acid.

The present invention relates to a recombinant expression "vector" comprising a polynucleotide encoding the endoglucanase polypeptide variants as characterized above, operably linked to regulatory sequences, which are capable of directing the expression of a gene encoding said endoglucanase polypeptide variants in a suitable host. Said regulatory sequences may originate from the host organism or from another organism. The expression vector may further comprise marker genes for selection of the transformant strains or the selection marker may be introduced to the host in another vector construct by co-transformation.

Still the present invention relates to a production "host", which can be any organism capable of expressing the desired polypeptide. Preferably the host is a microbial cell, more preferably a fungus. Most preferably the host is a filamentous fungus, such as *Trichoderma, Aspergillus, Fusarium, Humicola, Chrysosporium, Neurospora, Rhizopus, Penicillium, Myceliophthora, Sporotrichum*, and *Mortierella*. The endoglucanase polypeptide variants may be produced in a heterologous or homologous host. The host may or may not be genetically modified. Preferred hosts for producing the polypeptides of the invention are in particular strains from the genus *Trichoderma*. Preferably the recombinant host is modified to express and secrete the endoglucanase polypeptide variants of the invention as its main activity or one of its main activities. This can be done by deleting genes encoding major endogenous secreted enzymes e.g. the four major cellulases of *Trichoderma* and by integrating heterologous genes to a locus with high expression and production levels.

The present invention relates also to a method for producing variant endoglucanase polypeptides of the invention, said method comprising the steps of transforming a host cell with an expression vector encoding said polypeptide, and culturing said host cell under conditions enabling production of said polypeptide, and optionally recovering and purifying said polypeptide. The production medium may be a medium suitable for growing the host organism and containing inducers for efficient gene expression.

The present invention relates to an enzyme preparation comprising the variant endoglucanase polypeptides of the invention. As used in the present context the "enzyme preparation" refers to any enzyme product or composition, which comprises at least one of the novel variant endoglucanase polypeptides described herein. Such an enzyme preparation may be a spent culture medium or filtrate containing one or more variant endoglucanase polypeptides, or one or more variant endoglucanase polypeptides and one or more other enzymes. Spent culture medium means the culture medium of the host comprising the produced enzymes. Preferably the host cells are separated from said medium after the production. The enzyme preparation or composition may be a "whole culture broth" obtained, optionally after inactivating the production host(s) or microorganism(s) without any biomass separation, down-stream processing or purification of the desired cellulolytic enzyme(s), because the variant endoglucanase polypeptides can be secreted into the culture medium, and they display activity in the ambient conditions of the spent culture medium.

The enzyme preparation may contain the enzymes in at least partially purified and isolated form. It may even essentially consist of the desired enzyme or enzymes. If desired, the enzyme preparations may be dried, spray-dried or lyophilized, granulated or the enzymatic activity may be otherwise concentrated and/or stabilized for storage. If required, a desired enzyme may be crystallized or isolated or purified in accordance with conventional methods, such as filtration, extraction, precipitation, chromatography, affinity chromatography, electrophoresis, or the like.

In addition to one or more variant endoglucanase polypeptides, the enzyme preparation may comprise one or more other enzymes, which may be for example other cellulases, amylases, lipases, proteases, hemicellulases, ligninases, pectinolytic enzymes and/or oxidative enzymes. More specifically, the enzyme preparation may comprise at least one further enzyme selected from a group of cellobiohydrolase, endoglucanase, beta-glucanase, beta-glucosidase, serine protease, xylanase, beta-xylosidase, mannanase, beta-mannosidase, endopectinlyase, pectate lyase, pectinesterase, laccase, cutinase, peroxidase and copper-dependent lytic polysaccharide monooxygenase i.e. glycosyl hydrolase family 61 enzymes. The enzyme preparation may contain any combination of these enzymes and the variant endoglucanase polypeptides of the invention, but the enzymes are not limited to those described herein. They can for example also be commercially available enzyme preparations. It depends on the application what other enzymes are included in the enzyme preparation or used in the enzyme treatment.

In addition to the variant endoglucanase polypeptides, the enzyme preparation of the invention may comprise one or more suitable additives selected from the group consisting of surfactants or surface active agents, buffers, anti-corrosion agents, stabilizers, bleaching agents, mediators, builders, caustics, abrasives and preservatives, optical brighteners, antiredeposition agents, dyes, pigments, perfumes etc.

The enzyme preparations may be provided as a liquid or as a solid, for example, as a dried powder or granular, especially non-dusting granules, a stabilized liquid, tablet, crystal or crystal slurry. It is envisioned that the enzyme preparations can be further enriched to satisfy the requirements of a specific utility in various applications e.g. in the textile industry. A mixture of enzymes secreted by a host can be advantageous in a particular industrial application, for example in biofinishing and biostoning.

The present invention relates further to a detergent composition comprising at least one of the novel variant endoglucanase polypeptides or an enzyme preparation thereof, a surfactant and optionally one or more additives selected from the group consisting of stabilizers, buffers, surface active agents, builders, cobuilders, bleaching agents, bleach activators, other detergent enzymes, mediators of enzymes (e.g. for oxidases, peroxidases, laccases), anti-corrosion agents, antiredeposition agents and soil release polymers, caustics, abrasives, optical brighteners, dyes, pigments, perfumes and preservatives. As used in the present context, the expression "detergent" means a substance or material intended to assist cleaning or having cleaning properties. Suitable listing of the contents of detergents is given in U.S.

Pat. No. 5,443,750 or in WO2013/131964 and a suitable list of surfactants is given in U.S. Pat. No. 3,664,961.

Surfactants are useful in emulsifying grease and wetting surfaces. The surfactant may be a non-ionic including semipolar and/or anionic and/or cationic and/or zwitterionic. Buffers may be added to the enzyme preparation or composition to modify pH or affect performance or stability of other ingredients. Suitable stabilizers include polyols such as propylene glycol or glycerol, a sugar or sugar alcohol, lactic acid, boric acid, or boric acid derivatives, peptides, etc. Bleaching agent is used to oxidize and degrade organic compounds. Examples of suitable chemical bleaching systems are $H_2O_2$ sources, such as perborate or percarbonate with or without peracid-forming bleach activators such as tetraacetylethylenediamine, or alternatively peroxyacids, e.g. amide, imide or sulfone type. Chemical oxidizers may be replaced partially or completely by using oxidizing enzymes, such as laccases or peroxidases. Many laccases do not function effectively in the absence of mediators. Builders or complexing agents include substances, such as zeolite, diphosphate, triphosphate, carbonate, citrate, etc. The detergent composition may further comprise one or more polymers, such as carboxymethylcellulose, poly(ethylene glycol), poly(vinylalcohol), poly(vinylpyrrolidone), etc. Also, softeners, caustics, preservatives for preventing spoilage of other ingredients, abrasives and substances modifying the foaming and viscosity properties can be added.

The detergent composition of the invention may comprise one or more components selected from the group consisting of anionic surfactants (0-40% by weight), nonionic surfactants (0-40% by weight), and phosphonates (0-15% by weight) in addition to the effective amount of the variant endoglucanase polypeptide or an enzyme preparation thereof.

The term "effective amount" of an endoglucanase polypeptide variant refers to the quantity of the enzyme necessary to perform sufficiently in the specific detergent application. The amount of enzyme preparation in a detergent composition may vary depending on type and concentration of the detergent. Preferably the detergent composition comprises from about 0.00001% to about 10% by weight of the detergent composition of an endoglucanase polypeptide variant of the invention, more preferably from 0.0001% to about 1%, still more preferably from 0.0001% to 0.5%, even more preferably from 0.0005% to 0.1%. A person skilled in art is capable in defining suitable dosages.

An endoglucanase polypeptide variant or an enzyme preparation thereof may be added directly into a detergent or it can be applied separately on top of the detergent during or before wash, or, for example, in liquid/liquid or liquid/powder sachets or multicompartment sachets or bottles, in which it may be separated from some of the detergent components or other enzymes, like protease, to maximize the storage stability. An endoglucanase polypeptide variant or an enzyme preparation thereof can also be used in cleaning agents or boosters that are added on top of the detergent during or before the wash and that are for example in the form of liquid, gel, powder, granules or tablets. Enzyme preparation and detergent components may also be soaked in a carrier like textiles.

The variant endoglucanase polypeptides and the enzyme preparations thereof may be used for treating any cellulosic material. In the present context, "cellulosic material" refers to any material comprising cellulose or derivatives thereof as a significant component. Such a material may be textile material, plants or material of plant origin used in food or animal feed, plant material for oil extraction, or wood-derived mechanical or chemical pulp or secondary fiber.

The variant endoglucanase polypeptides are especially useful in the treatment of textile materials. The textile material to be treated may be any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, nonwovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, modal, cellulose acetate fibers (tricell), lyocell, cupro or blends thereof. Fabric may be conventional washable laundry, for example, stained household laundry. When the term fabric or garment is used it is intended to include the broader term textiles as well. By "denim" is meant, in connection of this invention, denim fabric, usually denim garments, particularly jeans. Advantageously, the denim is Indigo dyed denim. Denim can also be treated with derivatives of Indigo or with Indigo together with some other dye, for example, Indigo-dyed denim with sulphur bottom.

The cellulosic material is reacted with the variant endoglucanase polypeptides of the invention or the enzyme preparation comprising said variant endoglucanase polypeptides under suitable conditions, such as appropriate pH, and temperature, and the reaction is allowed to continue for a time sufficient for the enzymatic reaction to take place, whereby at least partially hydrolyzed cellulosic material is obtained. The enzymes are added in an enzymatically effective amount either simultaneously e.g. in the form of an enzyme mixture, or sequentially.

The variant endoglucanase polypeptides may also be added into detergent compositions to improve fiber and color care properties by prevention and removal of fuzz and pills resulting in brightening or freshening of colors and softening, and to improve textile cleaning, for instance by removal of pigment dirt and by antiredeposition and antigraying. Terms depilling (removal of pilling) and color revival are typically used to describe the cellulase effects on old, used cotton textiles. Terms antipilling (prevention of pilling), color maintenance or color care are typically used to describe cellulase effects on new garments.

As used in the present context the expression "cellulase performance" in detergent application refers to the effect of cellulase on the fiber and color care properties of detergent, that can be measured as a visible and measurable decrease of lightness (i.e. increase of darkness) or change in color of colored cotton textiles. When the surface fibers and fibrils protruding from the yarn forming pills and giving the fabric a greyish look are removed by cellulase, the lightness of the fabric decreases, and the surface of the fabric appears darker and colors get brighter. Lightness or change in color values can be measured, for example by measuring the color as reflectance values with a spectrophotometer using L*a*b* color space coordinates as described in Examples 4 and 6. Cellulase performance is for example calculated as $\Delta L^*$ (delta L*), which means lightness value L* of enzyme treated fabric minus lightness value L* of fabric treated with washing liquor without enzyme (enzyme blank, control). When the test material is consisting of textiles with different colors (e.g. commercially available pilling monitors containing 4 stripes), the total cellulase performance is calculated as a sum of ΔL* of each color after several washing cycles and the final results are shown as increase of darkness (sum of −ΔL*).

The variant endoglucanase polypeptides and the enzyme preparations containing them are especially useful in finishing processes of the textile industry, such as biofinishing of fabrics, garments or yarn. As used in the present context, the expression "biofinishing" (also called depilling, defuzzing, dehairing or biopolishing) refers to the use of the variant enzymes in a controlled hydrolysis of cellulosic fibers in order to modify the fabric or yarn surface in a manner that permanently prevents the tendency for pilling, improves fabric handle like softness and smoothness, clears the surface structure by reducing fuzzing. Biofinishing results in clarification of colors, improves the drapability of the fabric and improves moisture absorbability, which may further improve also the dyeability. Biofinishing may be performed before, after or at the same time as dyeing.

Enzymatic depilling can be carried out at any stage during textile wet processing, preferably after optional desizing and/or bleaching, and similar conditions as in biostoning can be used. Also textiles in garment form can be treated.

The variant endoglucanase polypeptides and enzyme preparations containing them may be used in biostoning of denim. As used in the present context, the expression "biostoning" of fabric or garment means the use of enzymes in place of, or in addition to, pumice stones for the treatment of fabric or garment, especially denim to obtain an aged or worn look. The term "aged or worn look" means that as a result of uneven dye removal, there are contrasts between dyed areas and areas from which dye has been removed.

The liquor ratio (the ratio of the volume of liquid per weight of fabric) in both biostoning and biofinishing may range from about 3:1 to 20:1, preferably 5:1 to 10:1. The treatment time can vary between 15 min to 90 min and preferably between 30 min to 60 min. It should be emphasized that the enzyme dosage greatly depends on the type of the fabrics, machinery, process conditions (pH, temperature, liquor ratio, treatment time, denim load, process scale) and type of the enzyme preparation or composition. Typical process parameters for e.g. industrial biofinishing are pH 4.5-8 at temperature of 40-65° C. The variant endoglucanase polypeptides of the invention show performance at a wide range of pH and temperature conditions. A person skilled in art is capable in defining suitable dosages and conditions.

The variant endoglucanase polypeptides of the invention and enzyme preparations or detergent compositions containing them provide unexpected advantages when used in detergent and textile industries. The novel variants are considerably more efficient than the cellulases of the prior art. In detergent applications, the novel variant endoglucanase polypeptides have considerably better color revival (pilling removal) and color care (antipilling) performance at lower dosing range. In biofinishing, high performance is achieved by using the variant endoglucanase polypeptides of the invention.

It will be obvious to a person skilled in the art that, as the technology advances, the inventive concept can be implemented in various ways. The invention and its embodiments are not limited to the examples described but may vary within the scope of the claims.

EXAMPLES

Example 1. Production of *Acremonium thermophilum* ACM0 Cellulase Variants in *Trichoderma reesei*

Standard molecular biology methods were used in isolation and enzyme treatments of DNA (plasmids, DNA fragments), in *E. coli* transformations, etc. The basic methods used are described in molecular biology handbooks, e.g. Sambrook J. and Russell, D. W., 2001.

Cellulase variants were derived from a parental molecule, designated here as cel45A-ACM0 (nucleic acid sequence SEQ ID NO: 3, corresponding to amino acid sequence SEQ ID NO: 12), containing the catalytic core of *A. thermophilum* Cel45A attached to the linker and CBM region of *T. reesei* Cel7A. Expression plasmids were constructed for production of recombinant ACM0 variants. The constructs contain *T. reesei* cel7A promoter and terminator and the amdS marker gene as described in Paloheimo et al., 2003. Synthetic genes (Table 1), including mutations introduced in the core region of the parental molecule, were exactly fused as SacII-BamHI fragments to the *T. reesei* cel7A promoter by ligation. For construction of the expression plasmid for ACM88 variant a 222 bp SgrAI fragment of pALK3923 was isolated and ligated into an 8859 bp SgrAI fragment of pALK3928. Expression plasmids are listed in Table 1.

TABLE 1

The synthetic genes used in construction of the expression cassettes for production of ACM0 cellulase variants in *T. reesei*

| Gene designation | Mutation | Expression plasmid | SEQ ID NO: |
|---|---|---|---|
| cel45A-ACM30 | S109N, S116Q, Q118H | pALK3675 | 4 |
| cel45A-ACM44 | S51N, S82Q, A135Q, S150Q, S205N | pALK3779 | 5 |
| cel45A-ACM72 | S51N, S82Q, S109N, S116E, Q118H, A135Q, S150Q, S205N | pALK3928 | 6 |
| cel45A-ACM86 | S51N, A75S, A77S, S82Q, S109N, Q118H, A135Q, S150Q, S205N | pALK3942 | 7 |
| cel45A-ACM88 | S51N, S82Q, S116E, Q118H, A135Q, S150Q, S205N | pALK3967 | 8 |

The linear expression cassette (FIG. 1) was isolated from the vector backbone by EcoRI digestion, transformed into *T. reesei* A152, and transformants were selected with acetamide as sole nitrogen source. The host strain lacks four major endogenous cellulases: CBHI/Cel7A, CBHII/Cel6A, EGI/Cel7B and EGII/Cel5A. The transformations were performed according to Penttila et al., 1987, with the modifications described in Karhunen et al., 1993. The transformants were purified on selection plates through single conidia prior to sporulating them on potato dextrose agar.

The endoglucanase production of the transformants was analyzed from the culture supernatants of shake flask cultivations (50 ml). The transformants were grown for 7 days in a complex cellulase-inducing medium (Joutsjoki et al., 1993) buffered with 5% $KH_2PO_4$ at pH 5.5. The enzyme activity of the recombinant protein was measured from the culture supernatant as the release of reducing sugars from carboxymethylcellulose (3% CMC) at 50° C. in 50 mM Sitrate buffer pH 4.8 essentially as described by Bailey, M. J. and Nevalainen, K. M. H., 1981; Haakana, H., et al., 2004. Production of the recombinant protein was also detected from the culture supernatant by sodium dodecyl sulfate polyacrylamide gel electrophoresis (SDS-PAGE).

The chosen transformants (Table 2) and the reference strain producing ACM0 cellulase were cultivated in laboratory scale bioreactors in complex cellulase-inducing medium to obtain material for the application tests (Examples 4 to 6).

TABLE 2

Transformants chosen for cultivation in
laboratory scale bioreactors

| Cellulase variant | Transformant |
|---|---|
| ACM30 | RF10612 |
| ACM44 | RF10834 |
| ACM72 | RF11193 |
| ACM86 | RF11081 |
| ACM88 | RF11217 |

Example 2. Production of *A. thermophilum* Cel45A Cellulase Variants in *T. reesei*

Standard molecular biology methods were used as described in Example 1. Two cellulase variants, derived from a parental molecule SEQ ID NO: 9 (corresponding to amino acid sequence SEQ ID NO: 13), were constructed. Expression plasmids (Table 3) were constructed by cloning synthetic genes and recombinant proteins were produced as described in Example 1.

TABLE 3

The synthetic genes used in construction of the expression
cassettes for production of At_Cel45A cellulase variants in *T. reesei*

| Gene designation | Mutation | Expression plasmid | SEQ ID NO: |
|---|---|---|---|
| cel45A-ACM90 | S51N, S82Q, S109N, S116E, Q118H, A135Q, S150Q, S205N | pALK3972 | 10 |
| cel45A-ACM91 | S51N, S82Q, S116E, Q118H, A135Q, S150Q, S205N | pALK3973 | 11 |

The endoglucanase production of the transformants was analyzed from the culture supernatants of shake flask cultivations (50 ml) as described in Example 1. The chosen transformants (Table 4) and the corresponding reference strain producing At_Cel45A cellulase were cultivated in laboratory scale bioreactors in complex cellulase-inducing medium to obtain material for the application tests (Examples 4 to 6).

TABLE 4

Transformants cultivated in laboratory scale bioreactors

| Cellulase variant | Transformant |
|---|---|
| ACM90 | RF11351 |
| ACM91 | RF11352 |

Example 3. Purification of Variant Endoglucanases

Cells and solids were removed from the fermentation culture medium by centrifugation for 10 min, 4000 g at 4° C. The supernatant of 15 ml was used for protein purification. After centrifugation, solid ammonium sulfate was added to the sample to obtain a final salt concentration of 1 M. The sample was then filtered through 0.44 µm filter before applying to phenyl Sepharose HiPrep 16/10 FF column (GE Healthcare) equilibrated with 20 mM MES, 1 M ammonium sulfate pH 6. The proteins were eluted with a linear decreasing ammonium sulfate gradient (from 1 to 0 M). Fractions of 10 ml were collected and analyzed on SDS-PAGE. The fractions containing endoglucanase activity were combined and concentrated to 2 ml using Vivaspin 20, 10 kDa MWCO ultrafiltration devices (GE Healthcare). The concentrated sample was further fractionated using Superdex 75 26/60 gel-filtration column equilibrated with 20 mM MES, 200 mM NaCl pH 6. Fractions of 2 ml were collected and analyzed by SDS-PAGE. Fractions containing pure endoglucanase were combined. Enzyme content of the purified sample was determined using UV absorbance 280 nm measurements. Excitation coefficients for the purified endoglucanases were calculated on the bases of amino acid sequence of the enzyme by using ExPASy Server http://web.expasy.org/protparam/.

The enzyme activity of purified samples was measured as the release of reducing sugars from carboxymethylcellulose (3% CMC) at 50° C. in 50 mM Hepes buffer pH 7.0 in 10 min (NCU activity), Bailey and Nevalainen, 1981; Haakana et al., 2004). The specific activity (NCU/mg) of enzyme variants was calculated by dividing NCU activity with the amount of purified enzyme. Obtained values were used for calculating enzyme dosages used in Examples 4 to 6.

Example 4. Launder-Ometer Tests of *A. thermophilum* ACM0 Cellulase Variants with Liquid Detergent Application

*A. thermophilum* ACM0 cellulase variants (ACM30, ACM44, ACM72, ACM86 and ACM88) produced in *Trichoderma*, as described in Example 1, were tested for their performance with Commercial liquid color detergent at 40° C. and compared to ACM0 cellulase and commercial cellulase preparation of Carezyme® (Cellulase of *Aspergillus* sp., Sigma-Aldrich C-2605-50 mL). The following pilling monitors (multicolor printed Jersey, 94% Cotton, 6% Dorlastan) supplied from Center For Testmaterials BV (The Netherlands) were used: E-252 (original fabric, unpilled) and E-253 (prepilled/predamaged material). Monitors E-253 were used for the demonstration of the removal of pilling (depilling) from material representing used cotton textiles. The same predamaged monitors were also used for demonstration of the color revival effect of used colored textiles. Monitors of original fabric (E-252) were used for the demonstration of the color maintenance/color care and/or prevention of pilling (antipilling) effect of new fabrics. Both test fabrics were cut into swatches (approx. 29 cm×15-16.5 cm, total weight of two swatches approx. 24 g) containing full width stripes of each color (black, red, green, blue) and the edges were neatened.

Cellulase treatments were performed in Atlas LP-2 Launder-Ometer as follows. Launder-Ometer was first preheated to 40° C. 60 g of steel balls (diameter 0.6 cm), 240 ml of wash liquor and diluted enzyme (<1.0 ml) were added into 1.2 liter containers. After that, one swatch of E-253 and E-252 were placed in containers (reverse side on reverse side) and the Launder-Ometer was run at 40° C. for 60 min with a rotation speed of 42 rpm.

Enzymes were dosed as mg of active enzyme protein (AEP). AEP content of each preparation was calculated on the basis of specific activities defined as described in Example 3. Dosage of the enzyme preparations was 0.2 or 0.1 mg of active enzyme protein per liter of wash liquor and control sample contained no enzyme. The wash liquor contained 5 g of Commercial liquid color detergent per liter of synthetic tap water (16° dH) and its pH was approx. 8.5.

For synthetic tap water with hardness of 16° dH the following stock solutions were prepared in deionized water (Milli-Q or equivalent):

Stock solution with 1000° d Calcium-hardness: $CaCl_2 \times 2$ $H_2O$ (1.02382.1000, Merck KGaA, Germany) 26.22 g/l Stock solution with 200° d Magnesium-hardness: $MgSO_4 \times 7$ $H_2O$ (1.05886.1000, Merck KGaA, Germany) 8.79 g/l $H_2O$ $NaHCO_3$ stock solution: $NaHCO_3$ (1.06329.1000 Merck KGaA, Germany) 29.6 g/l 13.3 ml $CaCl_2$ solution, 13.3 ml $MgSO_4$ solution and 10.0 ml of freshly made $NaHCO_3$ solution were added in volumetric flask in the given order, made up to 1 liter with deionized water and mixed. The hardness of water was determined by complexometric titration and found correct.

After the cellulase treatment in Launder-Ometer, the swatches were first rinsed separately under running water (ca. 20° C.) and then in a washing machine (Whirlpool) using rinsing program with extraction. Swatches were dried in a tumbler. Washing and tumbling cycles were repeated 10 times.

The cellulase performance in detergent application was evaluated by measuring the color of as reflectance values with Konica Minolta CM-3610A spectrophotometer using L*a*b* color space coordinates (illuminant D65/10°, 420 nm cut). The color of each 4 stripes of test monitors was measured after 10 washing cycles. Decrease of lightness (L*), i.e. increase of darkness compared to treatment without cellulase, was used as an indication of cellulase effect. When the surface fibers and fibrils protruding from the yarn forming pills and giving the fabric a greyish look are removed by cellulase, the lightness of the fabric decreases, and the surface of the fabric appears darker and colors get brighter.

Cellulase performance was calculated as ΔL* (delta L*), which means lightness value L* of enzyme treated fabric minus lightness value L* of fabric treated with washing liquor without enzyme (enzyme blank, control). Sum of ΔL* for each 4 stripes was calculated and the final results were shown as increase of darkness (−ΔL*).

Figure 2A:
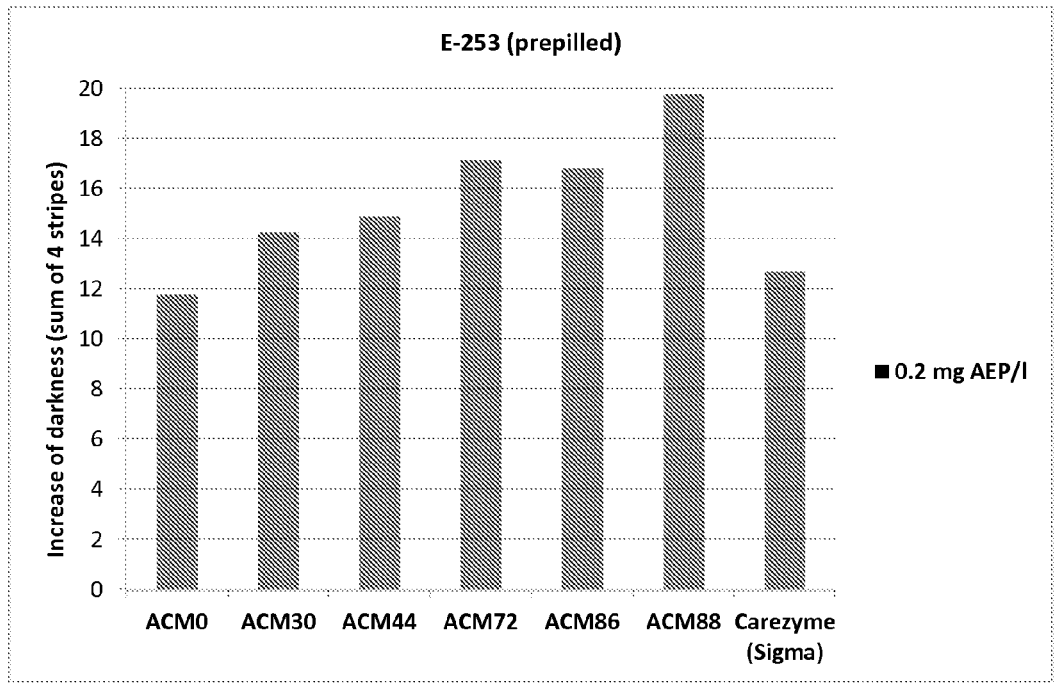
FIG. 2A shows results of prepilled test monitor E-253. Pilling removal/color revival effect.
Figure 2B:
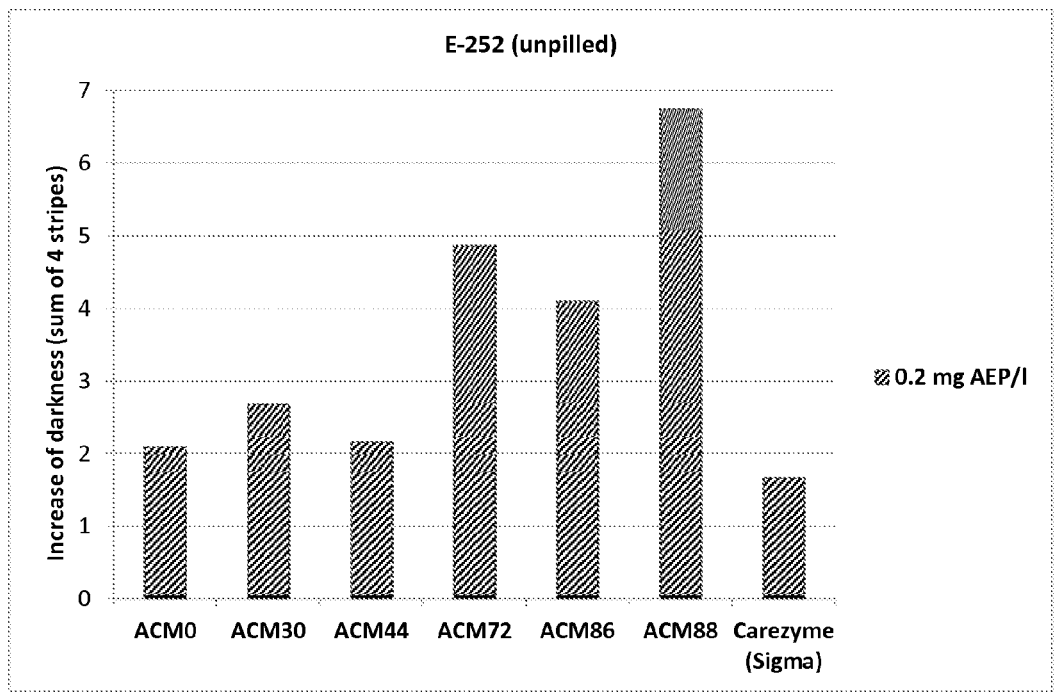
FIG. 2B shows results of unpilled test monitor (E-252). Color care/antipilling effect.
Figure 3A:
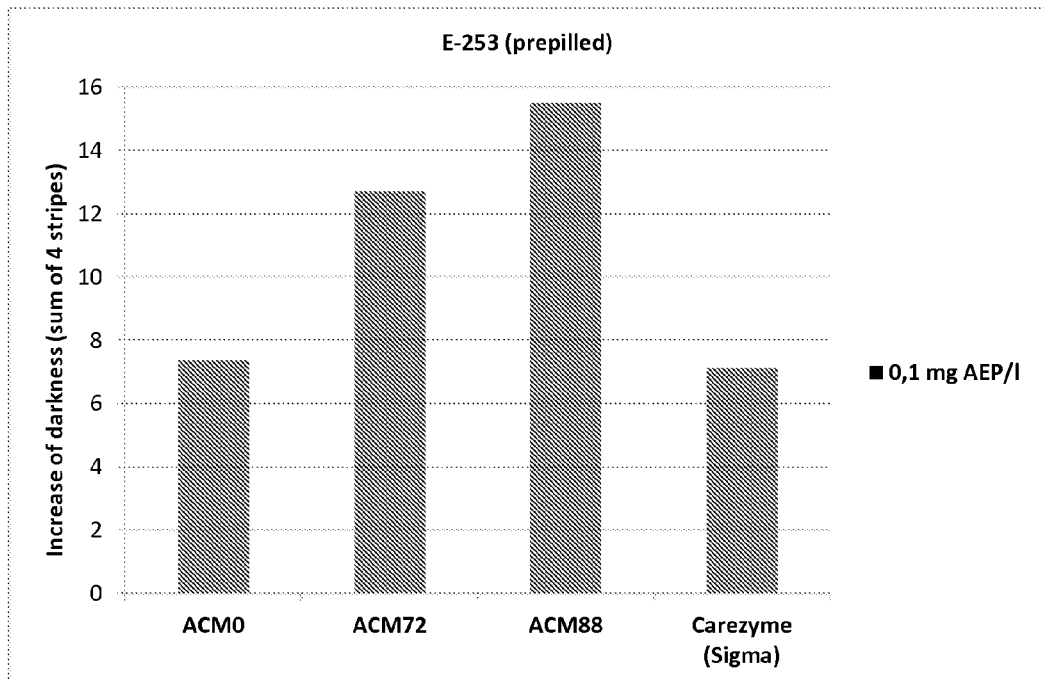
FIG. 3A shows results of prepilled test monitor E-253. Pilling removal/color revival effect.
Figure 3B:
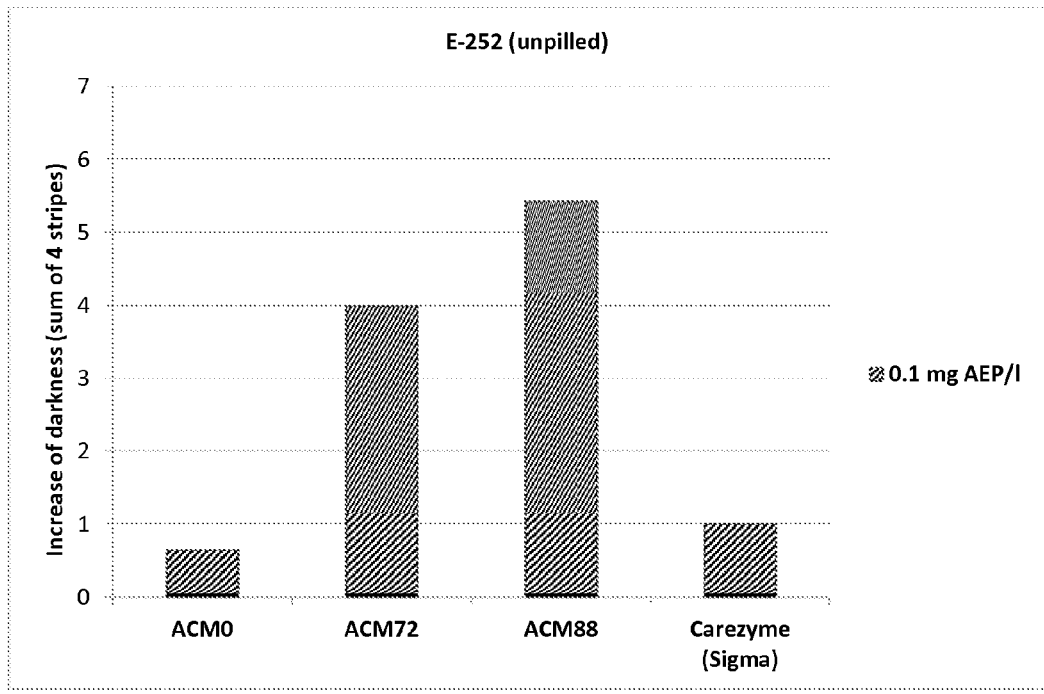
FIG. 3B shows results of unpilled test monitor (E-252). Color care/antipilling effect.

The results of the tests for increase of darkness using dosage 0.2 mg of active enzyme protein per liter of wash liquor are shown in FIGS. 2A (prepilled monitors E-253) and 2B (unpilled monitors E-252). Pilling removal/color revival effect (FIG. 2A) of variants ACM30, ACM44, ACM72, ACM86, and especially ACM88 was considerably improved as compared to ACM0. Also, the antipilling/color care effect of variants ACM30, ACM44, ACM72, ACM86, and especially ACM88 was better compared to ACM0. Variants ACM30, ACM44, ACM72, ACM86, and especially ACM88 had also better performance in detergent application than commercial reference Carezyme®. Furthermore, according to the tests performed with smaller dosage (0.1 mg of active enzyme protein per liter of wash liquor), as shown in FIG. 3, ACM72 and ACM88 had considerably better performance in detergent application with both prepilled (FIG. 3A) and unpilled (FIG. 3B) test monitors compared to ACM0 and commercial reference.

The spectrophotometrical results were also confirmed by visual evaluation. Prepilled/predamaged fabric, which appeared worn and uninteresting, regained its original look considerably better with ACM72 and especially with ACM88 compared to ACM0 and the commercial reference in both tests. Also the maintenance of colors of new fabric was visually clearly better with ACM72 and especially with ACM88 than with the references.

Example 5. Testing the Performance of *A. thermophilum* ACM0 Variants in Biofinishing Application The performance of *A. thermophilum* ACM0 variant ACM88 and ACM0 cellulase, produced in *Trichoderma*, as described in Example 1, was tested in biofinishing (depilling/defuzzing) of cotton knitwear. The cellulase treatments were performed with Electrolux's Wascator FOM 71 CLS washer extractor using 1 kg fabric and 15 liter of tap water. Rugged three yarn college knitwear made of 100% cotton (Type 9761, Orneule, Finland) was used as test material with filling material. The fabric was first prewashed for 10 min at 50° C. and rinsed 3 times. After that, the cotton knit fabric was treated with cellulase at 50° C. for 60 minutes. The enzymes were dosed as 0.025 or 0.05 mg of active enzyme protein (AEP) per the weight (g) of the fabric, as described in Example 4. pH of the washing liquid was adjusted to 6 with acetic acid or tests were performed without pH adjustment, when pH of the washing liquid was approx. 7.6 at start and 8 at the end of cellulase treatment. After draining, the enzyme was inactivated (for 10 min at 50° C.) by raising the pH above 11 with sodium hydroxide. The fabric was then rinsed three times and dried in a tumbler.

Figure 4:
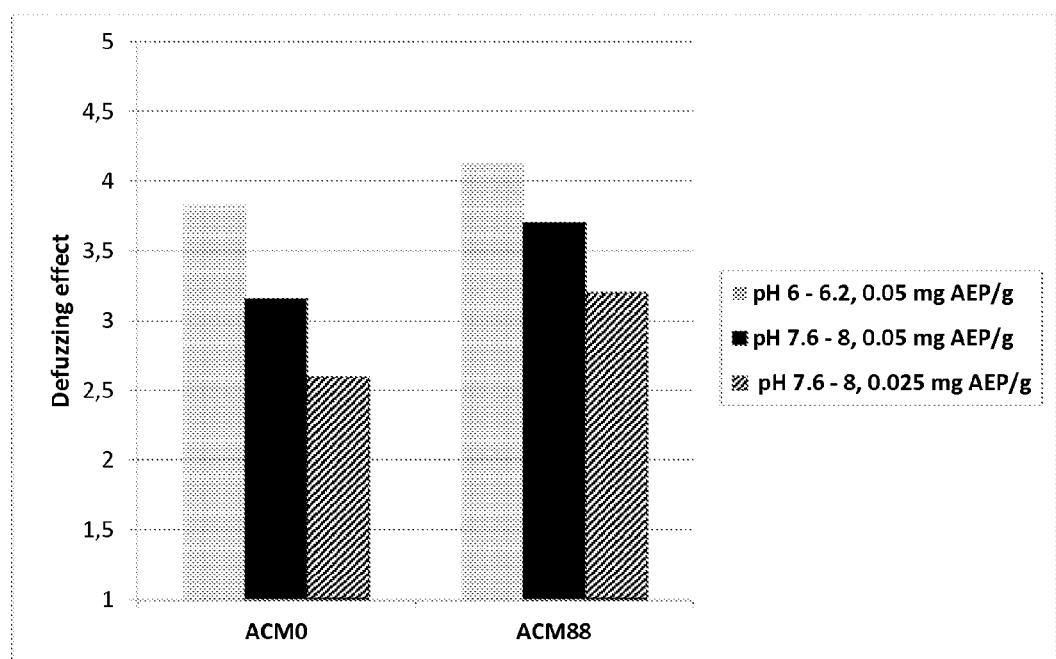
FIG. 4 shows the performance of *A. thermophilum* ACM0 variant ACM88 in biofinishing (defuzzing) treatment in washing machine at 50° C., pH 6 or without adjustment (pH approx. 8), 60 min, enzyme dosage 0.025 or 0.05 mg AEP per weight (g) of the fabric. The ACM0 cellulase was used for comparison.

The fabric samples were evaluated visually according to how much surface fibrils and fuzz was detected. The result of each evaluation was quantified by indicating the result relative to a scale consisting of standards. These standards were pieces of the same fabric washed with different amounts of cellulase and they had a range of intensity of surface fibrils/fuzz from number 1 to 5 with half unit's intervals. Number 1 was a control sample treated without enzyme. The higher the number, the better the defuzzing effect. The results are shown in FIG. 4. The biofinishing (defuzzing) performance of ACM88 variant was better than that of ACM0 at 50° C., both at pH 6 and without pH adjustment (pH approx. 8).

Example 6. Launder-Ometer Tests of *A. thermophilum* Cel45A Cellulase Variants with Liquid Detergent Application

*A. thermophilum* Cel45A cellulase variants ACM90 and ACM91 produced in *Trichoderma*, were tested for their performance with Commercial liquid color detergent at 40° C. and were compared to the At_Cel45A cellulase (SEQ ID NO: 13) and commercial cellulase preparation of Carezyme® (Sigma-Aldrich C-2605-50 mL).

The tests were performed and results evaluated as described in Example 3, except for that the dosages of At_Cel45A cellulase were 0, 0.1, 0.2 or 0.4 mg of active enzyme protein (AEP) per liter of wash liquor. The corresponding dosages of variant ACM90 or ACM91 were 0, 0.05, 0.1 or 0.2 mg of AEP/liter.

Figure 5A:
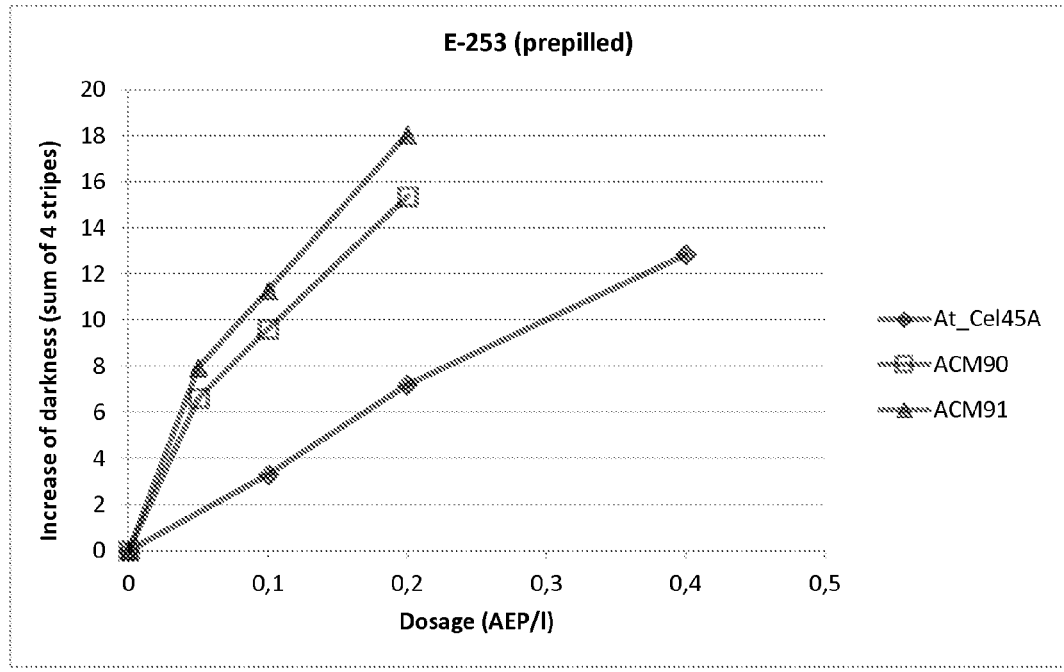
FIG. 5A shows results of prepilled test monitor E-253. Pilling removal/color revival effect.
Figure 5B:
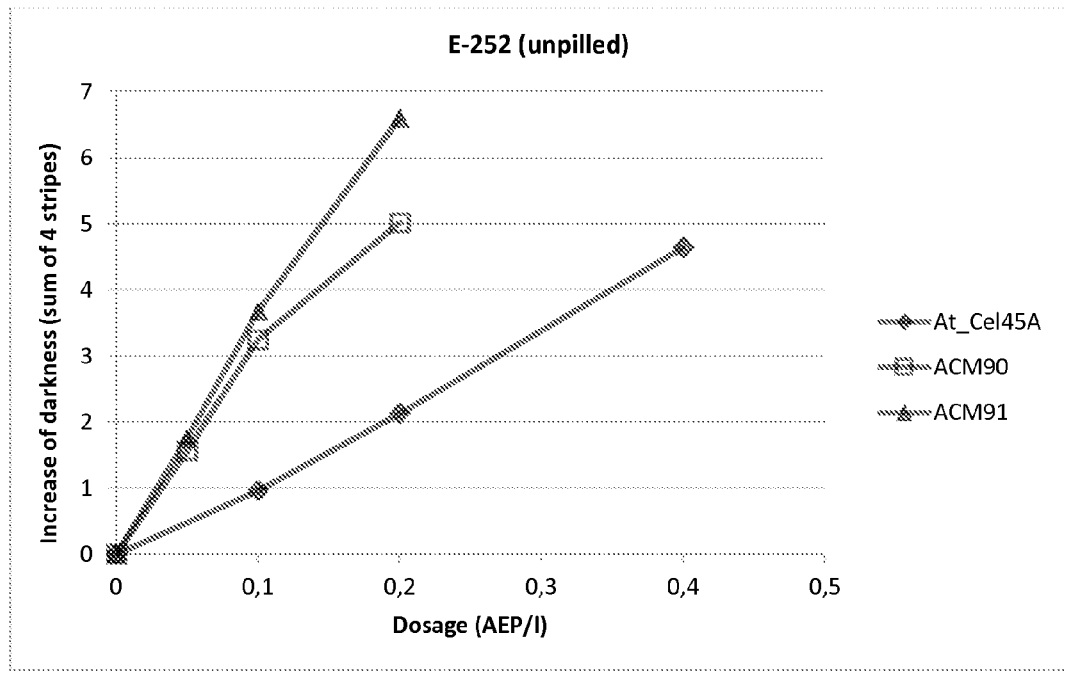
FIG. 5B shows results of unpilled test monitor (E-252). Color care/antipilling effect.

The results are shown in FIGS. 5A and B. The pilling removal/color revival effect measured with prepilled test monitor E-253 and antipilling/color care effect measured with unpilled monitor E-252 of variants ACM90 and ACM91 were considerably improved as compared to At_Cel45A cellulase.

As a conclusion, the results described in Examples 3 and 6 display that the performance of the endoglucanase variants is improved, as compared to the parental enzyme, regardless of the origin of the linker and the CBM region.

REFERENCES

Bailey M J and KMH Nevalainen 1981. Induction, isolation and testing of stable *Trichoderma reesei* mutants with improved production of solubilizing cellulase. Enz Microbiol Technol. 3: 153-157.

Coen D M. (2001) The polymerase chain reaction. In: Ausubel F M., Brent R., Kingston R E., More D D., Seidman J G., Smith K. and Struhl K. (eds.) Current protocols in molecular biology. John Wiley & Sons. Inc., Hoboken, USA.

Gellissen G. (ed.) (2005) Production of recombinant proteins. Novel microbial and eukaryotic expression systems. Wiley-VCH Verlag Gmbh&Co. Weinheim, Germany.

Haakana H, A Miettinen-Oinonen, V Joutsjoki, A Mäntylä, P Suominen, and J Vehmaanperä. 2004. Cloning of cellulase genes from *Melanocarpus albomyces* and their efficient expression in *Trichoderma reesei*. Enz Microbiol Technol. 34: 159-167.

Henrissat B. (1991) A classification of glycosyl hydrolases based on amino acid sequence similarities. Biochem. J. 280: 309-316.

Henrissat B. and Bairoch A. (1993) New families in the classification of glycosyl hydrolases based on amino acid sequence similarities. Biochem. J. 293: 781-788.

Henrissat B. and Bairoch A. (1996). Updating the sequence-based classification of glycosyl hydrolases. Biochem. J. 316: 695-696.

Joutsjoki, W, T K Torkkeli and KMH Nevalainen. 1993. Transformation of *Trichoderma reesei* with the *Hormoconis resinae* glucoamylase P (gamP) gene: production of a heterologous glucoamylase by *Trichoderma reesei*. Curr. Genet. 24:223-228.

Karhunen T, A Mäntylä, KMH Nevalainen and P L Suominen. 1993. High frequency one-step gene replacement in *Trichoderma reesei*. I. Endoglucanase I overproduction. Mol. Gen. Genet. 241:515-522.

Paloheimo M, A Mäntylä, J Kallio, and P Suominen. 2003. High-yield production of a bacterial xylanase in the filamentous fungus *Trichoderma reesei* requires a carrier polypeptide with an intact domain structure. Appl. Env. Microbiol. 69:7073-7082.

Penttilä M, H Nevalainen, M Rättö, E Salminen and J Knowles. 1987. A versatile transformation system for the cellulolytic filamentous fungus *Trichoderma reesei*. Gene 61:155-164.

Sambrook J and D W Russell. 2001. Molecular cloning, a laboratory manual. Cold Spring Harbor Laboratory, New York, US.

Smith T F and M S Waterman. 1981. Identification of common molecular subsequences. J. Mol. Biol. 147: 195-197.

The invention claimed is:

1. A variant endoglucanase polypeptide comprising an amino acid sequence having at least 95% sequence identity with amino acids 1 to 214 of SEQ ID NO: 1 and an amino acid substitution at three or more positions selected from the group consisting of 51, 75, 77, 82, 109, 116, 118, 135, 150 and 205, the positions being numbered with reference to SEQ ID NO: 1, wherein the variant polypeptide has endoglucanase activity.

2. The variant endoglucanase polypeptide of claim 1 attached to a carbohydrate binding module and optionally to a linker region.

3. The variant endoglucanase polypeptide of claim 1, wherein the variant endoglucanase polypeptide is attached to a carbohydrate binding module and a linker region, which are heterologous or homologous.

4. The variant endoglucanase polypeptide of claim 3, wherein at least one of the carbohydrate binding module and the linker region is heterologous.

5. The variant endoglucanase polypeptide of claim 1, wherein the polypeptide variant comprises a substitution at a position corresponding to three or more of S51N, A75S, A77S, S82Q, S109N, S116Q, S116E, Q118H, A135Q, S150Q or S205N.

6. The variant endoglucanase polypeptide of claim 1, wherein the polypeptide variant has a substitution at a position corresponding to S51N, S82Q, S109N, S116E, Q118H, A135Q, S150Q and S205N.

7. The variant endoglucanase polypeptide of claim 1, wherein the polypeptide variant has a substitution at a position corresponding to S51N, S82Q, S116E, Q118H, A135Q, S150Q and S205N.

8. The variant endoglucanase polypeptide of claim 1, wherein the polypeptide has an amino acid sequence of SEQ ID NO: 12 and an amino acid substitution at three or more positions selected from the group consisting of 51, 75, 77, 82, 109, 116, 118, 135, 150 and 205, the positions being numbered with reference to SEQ ID NO: 1.

9. The variant endoglucanase polypeptide of claim 1, wherein the polypeptide has an amino acid sequence of SEQ ID NO: 12 and an amino acid substitution at a position corresponding to S51N, S82Q, S109N, S116E, Q118H, A135Q, S150Q and S205N.

10. The variant endoglucanase polypeptide of claim 1, wherein the polypeptide has an amino acid sequence of SEQ ID NO: 12 and an amino acid substitution at a position corresponding to S51N, S82Q, S116E, Q118H, A135Q, S150Q and S205N.

11. An isolated polynucleotide comprising:
a) a polynucleotide or complementary DNA encoding an endoglucanase polypeptide variant of claim 1;
b) a polynucleotide encoding a fragment of a polypeptide encoded by a polynucleotide of a) wherein said fragment is having endoglucanase activity,
c) a polynucleotide comprising a nucleotide sequence which is degenerate to the nucleotide sequence of a polynucleotide sequence of a) or b),
or the complementary strand of such a polynucleotide.

12. A vector, which comprises an isolated polynucleotide of claim 11 operably linked to regulatory sequences capable of directing expression of the endoglucanase polypeptide variant.

13. A host cell comprising the vector of claim 12.

14. A method of producing the endoglucanase polypeptide variant of claim 1, said method comprising the steps of transforming a host cell with an expression vector encoding said polypeptide, and culturing said host cell under conditions enabling expression of said polypeptide, and optionally recovering and purifying said polypeptide variant.

15. An enzyme preparation comprising the endoglucanase polypeptide variant according to claim 1.

16. The enzyme preparation of claim 15 further comprising at least one enzyme selected from the group consisting of other cellulases, amylases, lipases, proteases, hemicellulases, ligninases, pectinolytic enzymes and oxidative enzymes.

17. A detergent composition comprising the endoglucanase polypeptide variant of claim 1 or an enzyme preparation thereof, a surfactant and optionally one or more additives selected from the group consisting of stabilizers, buffers, surface active agents, builders, cobuilders, bleaching agents, bleach activators, other detergent enzymes, mediators of oxidative enzymes, anti-corrosion agents, antiredeposition agents and soil release polymers, caustics, abrasives, optical brighteners, dyes, pigments, perfumes and preservatives.

18. A method for treating cellulosic material, wherein the method comprises reacting the cellulosic material with the endoglucanase polypeptide variant of claim 1 or an enzyme preparation thereof.

19. The method of claim 18, wherein the cellulosic material is textile material, plants used in animal feed, or wood-derived pulp or secondary fiber.

20. The method of claim 19, wherein the endoglucanase polypeptide variant is within a detergent composition and the detergent composition is contacted to the textile material.

21. The method of claim 18, wherein the cellulosic material is laundry which is subjected to biostoning or biofinishing.

* * * * *

```
                        SEQUENCE LISTING

<160> NUMBER OF SEQ ID NOS: 13

<210> SEQ ID NO 1
<211> LENGTH: 214
<212> TYPE: PRT
<213> ORGANISM: Acremonium thermophilum

<400> SEQUENCE: 1

Leu Asp Gly Lys Ser Thr Arg Tyr Trp Asp Cys Cys Lys Pro Ser Cys
1               5                   10                  15

Gly Trp Ala Gly Lys Ala Ser Val Asn Gln Pro Val Phe Ser Cys Ser
            20                  25                  30

Ala Asp Trp Gln Arg Ile Ser Asp Phe Asn Ala Lys Ser Gly Cys Asp
        35                  40                  45

Gly Gly Ser Ala Tyr Ser Cys Ala Asp Gln Thr Pro Trp Ala Val Asn
    50                  55                  60

Asp Asn Phe Ser Tyr Gly Phe Ala Ala Thr Ala Ile Ala Gly Gly Ser
65                  70                  75                  80

Glu Ser Ser Trp Cys Cys Ala Cys Tyr Ala Leu Thr Phe Asn Ser Gly
                85                  90                  95

Pro Val Ala Gly Lys Thr Met Val Val Gln Ser Thr Ser Thr Gly Gly
            100                 105                 110

Asp Leu Gly Ser Asn Gln Phe Asp Leu Ala Ile Pro Gly Gly Gly Val
        115                 120                 125

Gly Ile Phe Asn Gly Cys Ala Ser Gln Phe Gly Gly Leu Pro Gly Ala
    130                 135                 140

Gln Tyr Gly Gly Ile Ser Asp Arg Ser Gln Cys Ser Ser Phe Pro Ala
145                 150                 155                 160

Pro Leu Gln Pro Gly Cys Gln Trp Arg Phe Asp Trp Phe Gln Asn Ala
                165                 170                 175

Asp Asn Pro Thr Phe Thr Phe Gln Arg Val Gln Cys Pro Ser Glu Leu
            180                 185                 190

Thr Ser Arg Thr Gly Cys Lys Arg Asp Asp Ala Ser Tyr Pro Val
        195                 200                 205

Phe Asn Pro Pro Ser Gly
    210
```

<210> SEQ ID NO 2
<211> LENGTH: 214
<212> TYPE: PRT
<213> ORGANISM: Geomyces pannorum

<400> SEQUENCE: 2

```
Ala Ser Gly Asn Gly Lys Thr Thr Arg Tyr Trp Asp Cys Cys Lys Pro
1               5                   10                  15

Ser Cys Ala Trp Ser Gly Lys Ala Ser Phe Lys Thr Gly Pro Val Gln
            20                  25                  30

Ser Cys Asp Lys Gly Asp Asn Val Leu Ala Asp Ala Asp Thr Lys Ser
        35                  40                  45

Ala Cys Asp Asn Gly Gly Pro Ala Phe Met Cys Ser Asp Glu Ser Pro
    50                  55                  60

Trp Ala Val Ser Asp Ser Leu Ala Tyr Gly Phe Ala Ala Val Ser Ile
65                  70                  75                  80

Ser Gly Gly Thr Glu Ala Ser Trp Cys Cys Ala Cys Tyr Glu Leu Thr
                85                  90                  95

Phe Thr Ser Gly Pro Val Ser Gly Lys Lys Met Val Val Gln Ala Thr
            100                 105                 110

Asn Thr Gly Gly Asp Leu Gly Gln Asn His Phe Asp Ile Gly Met Pro
        115                 120                 125

Gly Gly Gly Phe Gly Leu Phe Asn Ala Cys Thr Pro Gln Tyr Gly Thr
    130                 135                 140

Pro Ser Thr Gly Trp Gly Asn Gln Tyr Gly Gly Leu Thr Ser Arg Ser
145                 150                 155                 160

Gln Cys Asp Ala Phe Pro Gln Ala Leu Lys Ala Gly Cys Tyr Trp Arg
                165                 170                 175

Phe Asp Trp Phe Gln Asn Ala Asp Asn Pro Ser Val Ser Phe Lys Ser
            180                 185                 190

Val Ala Cys Pro Leu Ala Leu Thr Asn Lys Ser Gly Cys Val Arg Ser
        195                 200                 205

Asp Asp Thr Pro Thr Gly
    210
```

<210> SEQ ID NO 3
<211> LENGTH: 1079
<212> TYPE: DNA
<213> ORGANISM: Acremonium thermophilum

<400> SEQUENCE: 3

| | |
|---|---:|
| atgtatcgga agttggccgt catctcggcc ttcttggcca cagctcgtgc cctcgacgga | 60 |
| aagtcgacga ggtatgccaa tcctcgtacc tctgccctct gtagaaacaa gtgaccgact | 120 |
| gcaaagacag atactgggac tgctgcaagc cgtcctgcgg ctgggccgga aaggcctcgg | 180 |
| tgaaccagcc cgtcttctcg tgctcggccg actggcagcg catcagcgac ttcaacgcga | 240 |
| agtcgggctg cgacggaggc tccgcctact cgtgcgccga ccagacgccc tgggcggtca | 300 |
| acgacaactt ctcgtacggc ttcgcagcca cggccatcgc cggcggctcc gagtccagct | 360 |
| ggtgctgcgc ctgctatgcg tgagttctct gcaagccgct tcccaccccc gctttctgtg | 420 |
| caggccgctt ccccccctacc cacccacttc cccccccccg cctctgtgat cgggcatccg | 480 |
| agctaagttg cgtgtcgtcc agactcacct tcaactcggg cccgtcgcg gcaagacca | 540 |
| tggtggtgca gtcgaccagc accggcggcg acctgggcag caaccagttc gacctcgcca | 600 |

```
tccccggcgg cggcgtgggc atcttcaacg gctgcgcctc ccagttcggc ggcctccccg    660
gcgcccagta cggcggcatc agcgaccgca gccagtgctc gtccttcccc gcgccgctcc    720
agccgggctg ccagtggcgc ttcgactggt tccagaacgc cgacaacccc accttcacct    780
tccagcgcgt gcagtgcccg tccgagctca cgtcccgcac gggctgtaag cgcgacgacg    840
acgccagcta tcccgtcttc aacccgcctt cgggcaaccc tagcggcggc aaccctcccg    900
gcggaaaccc gcctggcacc accaccaccc gccgcccagc cactaccact ggaagctctc    960
ccggacctac ccagtctcac tacggccagt gcggcggtat tggctacagc ggccccacgg    1020
tctgcgccag cggcacaact tgccaggtcc tgaaccctta ctactctcag tgcctgtaa    1079
```

<210> SEQ ID NO 4
<211> LENGTH: 1079
<212> TYPE: DNA
<213> ORGANISM: Acremonium thermophilum

<400> SEQUENCE: 4

```
atgtatcgga agttggccgt catctcggcc ttcttggcca cagctcgtgc cctcgacgga     60
aagtcgacga ggtatgccaa tcctcgtacc tctgccctct gtagaaacaa gtgaccgact    120
gcaaagacag atactgggac tgctgcaagc cgtcctgcgg ctgggccgga aaggcctcgg    180
tgaaccagcc cgtcttctcg tgctcggccg actggcagcg catcagcgac ttcaacgcga    240
agtcgggctg cgacgaggc tccgcctact cgtgcgccga ccagacgccc tgggcggtca    300
acgacaactt ctcgtacggc ttcgcagcca cggccatcgc cggcggctcc gagtccagct    360
ggtgctgcgc ctgctatgcg tgagttctct gcaagccgct tcccaccccc gctttctgtg    420
caggccgctt ccccctacc caccactttc ccccccccg cctctgtgat cgggcatccg    480
agctaagttg cgtgtcgtcc agactcacct tcaactcggg cccgtcgcg ggcaagacca    540 tggtggtgca gtcgaccaac accggcggcg acctgggcca gaaccacttc gacctcgcca    600
tccccggcgg cggcgtgggc atcttcaacg gctgcgcctc ccagttcggc ggcctccccg    660
gcgcccagta cggcggcatc agcgaccgca gccagtgctc gtccttcccc gcgccgctcc    720
agccgggctg ccagtggcgc ttcgactggt tccagaacgc cgacaacccc accttcacct    780
tccagcgcgt gcagtgcccg tccgagctca cgtcccgcac gggctgtaag cgcgacgacg    840
acgccagcta tcccgtcttc aacccgcctt cgggcaaccc tagcggcggc aaccctcccg    900
gcggaaaccc gcctggcacc accaccaccc gccgcccagc cactaccact ggaagctctc    960
ccggacctac ccagtctcac tacggccagt gcggcggtat tggctacagc ggccccacgg    1020
tctgcgccag cggcacaact tgccaggtcc tgaaccctta ctactctcag tgcctgtaa    1079
```

<210> SEQ ID NO 5
<211> LENGTH: 1079
<212> TYPE: DNA
<213> ORGANISM: Acremonium thermophilum

<400> SEQUENCE: 5

```
atgtatcgga agttggccgt catctcggcc ttcttggcca cagctcgtgc cctcgacgga     60
aagtcgacga ggtatgccaa tcctcgtacc tctgccctct gtagaaacaa gtgaccgact    120
gcaaagacag atactgggac tgctgcaagc cgtcctgcgg ctgggccgga aaggcctcgg    180
tgaaccagcc cgtcttctcg tgctcggccg actggcagcg catcagcgac ttcaacgcga    240
agtcgggctg cgacgaggc aacgcctact cgtgcgccga ccagacgccc tgggcggtca    300
acgacaactt ctcgtacggc ttcgcagcca cggccatcgc cggcggctcc gagcagagct    360
```

```
ggtgctgcgc ctgctatgcg tgagttctct gcaagccgct cccaccccc gctttctgtg    420 caggccgctt ccccctacc cacccacttc ccccccccg cctctgtgat cgggcatccg    480
agctaagttg cgtgtcgtcc agactcacct tcaactcggg cccgtcgcg ggcaagacca    540 tggtggtgca gtcgaccagc accggcggcg acctgggcag caaccagttc gacctcgcca    600
tccccggcgg cggcgtgggc atcttcaacg gctgccagtc ccagttcggc ggcctccccg    660
gcgcccagta cggcggcatc caggaccgca gccagtgctc gtccttcccc gcgccgctcc    720
agccgggctg ccagtggcgc ttcgactggt tccagaacgc cgacaacccc accttcacct    780
tccagcgcgt gcagtgcccg tccgagctca cgtcccgcac gggctgtaag cgcgacgacg    840
acgccaacta tcccgtcttc aacccgcctt cgggcaaccc tagcggcggc aaccctcccg    900
gcggaaaccc gcctggcacc accaccaccc gccgcccagc cactaccact ggaagctctc    960
ccggacctac ccagtctcac tacggccagt gcggcggtat tggctacagc ggccccacgg    1020
tctgcgccag cggcacaact tgccaggtcc tgaaccctta ctactctcag tgcctgtaa    1079
```

<210> SEQ ID NO 6
<211> LENGTH: 1079
<212> TYPE: DNA
<213> ORGANISM: Acremonium thermophilum

<400> SEQUENCE: 6

```
atgtatcgga agttggccgt catctcggcc ttcttggcca cagctcgtgc cctcgacgga     60
aagtcgacga ggtatgccaa tcctcgtacc tctgccctct gtagaaacaa gtgaccgact    120
gcaaagacag atactgggac tgctgcaagc cgtcctgcgg ctgggccgga aaggcctcgg    180
tgaaccagcc cgtcttctcg tgctcggccg actggcagcg catcagcgac ttcaacgcga    240
agtcgggctg cgacggaggc aacgcctact cgtgcgccga ccagacgccc tgggcggtca    300
acgacaactt ctcgtacggc ttcgcagcca cggccatcgc cggcggctcc gagcagagct    360
ggtgctgcgc ctgctatgcg tgagttctct gcaagccgct cccaccccc gctttctgtg    420 caggccgctt ccccctacc cacccacttc ccccccccg cctctgtgat cgggcatccg    480
agctaagttg cgtgtcgtcc agactcacct tcaactcggg cccgtcgcg ggcaagacca    540 tggtggtgca gtcgaccaac accggcggcg acctgggcga gaaccacttc gacctcgcca    600
tccccggcgg cggcgtgggc atcttcaacg gctgccagtc ccagttcggc ggcctccccg    660
gcgcccagta cggcggcatc caggaccgca gccagtgctc gtccttcccc gcgccgctcc    720
agccgggctg ccagtggcgc ttcgactggt tccagaacgc cgacaacccc accttcacct    780
tccagcgcgt gcagtgcccg tccgagctca cgtcccgcac gggctgtaag cgcgacgacg    840
acgccaacta tcccgtcttc aacccgcctt cgggcaaccc tagcggcggc aaccctcccg    900
gcggaaaccc gcctggcacc accaccaccc gccgcccagc cactaccact ggaagctctc    960
ccggacctac ccagtctcac tacggccagt gcggcggtat tggctacagc ggccccacgg    1020
tctgcgccag cggcacaact tgccaggtcc tgaaccctta ctactctcag tgcctgtaa    1079
```

<210> SEQ ID NO 7
<211> LENGTH: 1079
<212> TYPE: DNA
<213> ORGANISM: Acremonium thermophilum

<400> SEQUENCE: 7

```
atgtatcgga agttggccgt catctcggcc ttcttggcca cagctcgtgc cctcgacgga     60
```

-continued

| | | | |
|---|---|---|---|
| aagtcgacga | ggtatgccaa | tcctcgtacc tctgccctct gtagaaacaa gtgaccgact | 120 |
| gcaaagacag | atactgggac | tgctgcaagc cgtcctgcgg ctgggccgga aaggcctcgg | 180 |
| tgaaccagcc | cgtcttctcg | tgctcggccg actggcagcg catcagcgac ttcaacgcga | 240 |
| agtcgggctg | cgacggaggc | aacgcctact cgtgcgccga ccagacgccc tgggcggtca | 300 |
| acgacaactt | ctcgtacggc | ttcgcagcca cgtccatctc cggcggctcc gagcagagct | 360 |
| ggtgctgcgc | ctgctatgcg | tgagttctct gcaagccgct tcccacccccc gctttctgtg | 420 |
| caggccgctt | cccccctacc | cacccacttc ccccccccg cctctgtgat cgggcatccg | 480 |
| agctaagttg | cgtgtcgtcc | agactcacct tcaactcggg cccgtcgcg ggcaagacca | 540 |
| tggtggtgca | gtcgaccaac | accggcggcg acctgggcag caaccacttc gacctcgcca | 600 |
| tccccggcgg | cggcgtgggc | atcttcaacg gctgccagtc ccagttcggc ggcctccccg | 660 |
| gcgcccagta | cggcggcatc | caggaccgca gccagtgctc gtccttcccc gcgccgctcc | 720 |
| agccgggctg | ccagtggcgc | ttcgactggt tccagaacgc cgacaacccc accttcacct | 780 |
| tccagcgcgt | gcagtgcccg | tccgagctca cgtcccgcac gggctgtaag cgcgacgacg | 840 |
| acgccaacta | tcccgtcttc | aacccgcctt cgggcaaccc tagcggcggc aaccctcccg | 900 |
| gcggaaaccc | gcctggcacc | accaccaccc gccgcccagc cactaccact ggaagctctc | 960 |
| ccggacctac | ccagtctcac | tacgccagt gcggcggtat tggctacagc ggccccacgg | 1020 |
| tctgcgccag | cggcacaact | tgccaggtcc tgaaccctta ctactctcag tgcctgtaa | 1079 |

<210> SEQ ID NO 8
<211> LENGTH: 1079
<212> TYPE: DNA
<213> ORGANISM: Acremonium thermophilum

<400> SEQUENCE: 8

| | | | |
|---|---|---|---|
| atgtatcgga | agttggccgt | catctcggcc ttcttggcca cagctcgtgc cctcgacgga | 60 |
| aagtcgacga | ggtatgccaa | tcctcgtacc tctgccctct gtagaaacaa gtgaccgact | 120 |
| gcaaagacag | atactgggac | tgctgcaagc cgtcctgcgg ctgggccgga aaggcctcgg | 180 |
| tgaaccagcc | cgtcttctcg | tgctcggccg actggcagcg catcagcgac ttcaacgcga | 240 |
| agtcgggctg | cgacggaggc | aacgcctact cgtgcgccga ccagacgccc tgggcggtca | 300 |
| acgacaactt | ctcgtacggc | ttcgcagcca cggccatcgc cggcggctcc gagcagagct | 360 |
| ggtgctgcgc | ctgctatgcg | tgagttctct gcaagccgct tcccacccccc gctttctgtg | 420 |
| caggccgctt | cccccctacc | cacccacttc ccccccccg cctctgtgat cgggcatccg | 480 |
| agctaagttg | cgtgtcgtcc | agactcacct tcaactcggg cccgtcgcg gcaagacca | 540 |
| tggtggtgca | gtcgaccagc | accggcggcg acctgggcga gaaccacttc gacctcgcca | 600 |
| tccccggcgg | cggcgtgggc | atcttcaacg gctgccagtc ccagttcggc ggcctccccg | 660 |
| gcgcccagta | cggcggcatc | caggaccgca gccagtgctc gtccttcccc gcgccgctcc | 720 |
| agccgggctg | ccagtggcgc | ttcgactggt tccagaacgc cgacaacccc accttcacct | 780 |
| tccagcgcgt | gcagtgcccg | tccgagctca cgtcccgcac gggctgtaag cgcgacgacg | 840 |
| acgccaacta | tcccgtcttc | aacccgcctt cgggcaaccc tagcggcggc aaccctcccg | 900 |
| gcggaaaccc | gcctggcacc | accaccaccc gccgcccagc cactaccact ggaagctctc | 960 |
| ccggacctac | ccagtctcac | tacgccagt gcggcggtat tggctacagc ggccccacgg | 1020 |
| tctgcgccag | cggcacaact | tgccaggtcc tgaaccctta ctactctcag tgcctgtaa | 1079 |

<210> SEQ ID NO 9
<211> LENGTH: 1076
<212> TYPE: DNA
<213> ORGANISM: Acremonium thermophilum

<400> SEQUENCE: 9

| | | | | | |
|---|---|---|---|---|---|
| atgcgctcct | cacccttct | ccgcgcagct | ctggctgccg | ctctgcctct | gagcgcccat | 60 |
| gccctcgacg | gaaagtcgac | gaggtatgcc | aatcctcgta | cctctgccct | ctgtagaaac | 120 |
| aagtgaccga | ctgcaaagac | agatactggg | actgctgcaa | gccgtcctgc | ggctgggccg | 180 |
| gaaaggcctc | ggtgaaccag | cccgtcttct | cgtgctcggc | cgactggcag | cgcatcagcg | 240 |
| acttcaacgc | gaagtcgggc | tgcgacgag | gctccgccta | tcgtgcgcc | gaccagacgc | 300 |
| cctgggcggt | caacgacaac | ttctcgtacg | gcttcgcagc | cacggccatc | gccggcggct | 360 |
| ccgagtccag | ctggtgctgc | gcctgctatg | cgtgagttct | ctgcaagccg | cttcccaccc | 420 |
| ccgctttctg | tgcaggccgc | ttcccccta | cccacccact | tcccccccc | cgcctctgtg | 480 |
| atcgggcatc | cgagctaagt | tgcgtgtcgt | ccagactcac | cttcaactcg | gccccgtcg | 540 |
| cgggcaagac | catggtggtg | cagtcgacca | gcaccggcgg | cgacctgggc | agcaaccagt | 600 |
| tcgacctcgc | catccccggc | ggcggcgtgg | gcatcttcaa | cggctgcgcc | tcccagttcg | 660 |
| gcggcctccc | cggcgcccag | tacggcggca | tcagcgaccg | cagccagtgc | tcgtccttcc | 720 |
| ccgcgccgct | ccagcgggc | tgccagtggc | gcttcgactg | gttccagaac | gccgacaacc | 780 |
| ccaccttcac | cttccagcgc | gtgcagtgcc | cgtccgagct | cacgtcccgc | acgggctgta | 840 |
| agcgcgacga | cgacgccagc | tatcccgtct | tcaacccgcc | tagcggtggc | tcccccagca | 900 |
| ccaccagcac | caccaccagc | tccccgtccg | gtcccacggg | caaccctcct | ggaggcggtg | 960 |
| gctgcactgc | ccagaagtgg | gcccagtgcg | gcggcactgg | cttcacgggc | tgcaccacct | 1020 |
| gcgtctcggg | caccacctgc | caggtgcaga | accagtggta | ttcccagtgt | ctgtga | 1076 |

<210> SEQ ID NO 10
<211> LENGTH: 1076
<212> TYPE: DNA
<213> ORGANISM: Acremonium thermophilum

<400> SEQUENCE: 10

| | | | | | |
|---|---|---|---|---|---|
| atgcgctcct | cacccttct | ccgcgcagct | ctggctgccg | ctctgcctct | gagcgcccat | 60 |
| gccctcgacg | gaaagtcgac | gaggtatgcc | aatcctcgta | cctctgccct | ctgtagaaac | 120 |
| aagtgaccga | ctgcaaagac | agatactggg | actgctgcaa | gccgtcctgc | ggctgggccg | 180 |
| gaaaggcctc | ggtgaaccag | cccgtcttct | cgtgctcggc | cgactggcag | cgcatcagcg | 240 |
| acttcaacgc | gaagtcgggc | tgcgacggag | gcaacgccta | tcgtgcgcc | gaccagacgc | 300 |
| cctgggcggt | caacgacaac | ttctcgtacg | gcttcgcagc | cacggccatc | gccggcggct | 360 |
| ccgagcagag | ctggtgctgc | gcctgctatg | cgtgagttct | ctgcaagccg | cttcccaccc | 420 |
| ccgctttctg | tgcaggccgc | ttcccccta | cccacccact | tcccccccc | cgcctctgtg | 480 |
| atcgggcatc | cgagctaagt | tgcgtgtcgt | ccagactcac | cttcaactcg | gccccgtcg | 540 |
| cgggcaagac | catggtggtg | cagtcgacca | acaccggcgg | cgacctgggc | gagaaccact | 600 |
| tcgacctcgc | catccccggc | ggcggcgtgg | gcatcttcaa | cggctgccag | tcccagttcg | 660 |
| gcggcctccc | cggcgcccag | tacggcggca | tccaggaccg | cagccagtgc | tcgtccttcc | 720 |
| ccgcgccgct | ccagcgggc | tgccagtggc | gcttcgactg | gttccagaac | gccgacaacc | 780 |
| ccaccttcac | cttccagcgc | gtgcagtgcc | cgtccgagct | cacgtcccgc | acgggctgta | 840 |

```
agcgcgacga cgacgccaac tatcccgtct tcaacccgcc tagcggtggc tcccccagca    900
ccaccagcac caccaccagc tccccgtccg gtcccacggg caaccctcct ggaggcggtg    960
gctgcactgc ccagaagtgg gcccagtgcg gcggcactgg cttcacgggc tgcaccacct   1020
gcgtctcggg caccacctgc caggtgcaga accagtggta ttcccagtgt ctgtga       1076

<210> SEQ ID NO 11
<211> LENGTH: 1076
<212> TYPE: DNA
<213> ORGANISM: Acremonium thermophilum

<400> SEQUENCE: 11
atgcgctcct caccctttct ccgcgcagct ctggctgccg ctctgcctct gagcgcccat     60
gccctcgacg gaaagtcgac gaggtatgcc aatcctcgta cctctgccct ctgtagaaac    120
aagtgaccga ctgcaaagac agatactggg actgctgcaa gccgtcctgc ggctgggccg    180
gaaaggcctc ggtgaaccag cccgtcttct cgtgctcggc cgactggcag cgcatcagcg    240
acttcaacgc gaagtcgggc tgcgacggag gcaacgccta ctcgtgcgcc gaccagacgc    300
cctgggcggt caacgacaac ttctcgtacg gcttcgcagc cacggccatc gccggcggct    360
ccgagcagag ctggtgctgc gcctgctatg cgtgagttct ctgcaagccg cttcccaccc    420 ccgcttctg tgcaggccgc ttccccccta cccacccact tccccccccc cgcctctgtg    480
atcgggcatc cgagctaagt tgcgtgtcgt ccagactcac cttcaactcg gccccgtcg    540 cgggcaagac catggtggtg cagtcgacca gcaccggcgg cgacctgggc gagaaccact    600
tcgacctcgc catccccggc ggcggcgtgg gcatcttcaa cggctgccag tcccagttcg    660
gcggcctccc cggcgcccag tacggcggca tccaggaccg cagccagtgc tcgtccttcc    720
ccgcgccgct ccagccgggc tgccagtggc gcttcgactg gttccagaac gccgacaacc    780
ccaccttcac cttccagcgc gtgcagtgcc cgtccgagct cacgtcccgc acgggctgta    840
agcgcgacga cgacgccaac tatcccgtct tcaacccgcc tagcggtggc tcccccagca    900
ccaccagcac caccaccagc tccccgtccg gtcccacggg caaccctcct ggaggcggtg    960
gctgcactgc ccagaagtgg gcccagtgcg gcggcactgg cttcacgggc tgcaccacct   1020
gcgtctcggg caccacctgc caggtgcaga accagtggta ttcccagtgt ctgtga       1076

<210> SEQ ID NO 12
<211> LENGTH: 298
<212> TYPE: PRT
<213> ORGANISM: Acremonium thermophilum

<400> SEQUENCE: 12

Met Tyr Arg Lys Leu Ala Val Ile Ser Ala Phe Leu Ala Thr Ala Arg
1               5                   10                  15

Ala Leu Asp Gly Lys Ser Thr Arg Tyr Trp Asp Cys Cys Lys Pro Ser
                20                  25                  30

Cys Gly Trp Ala Gly Lys Ala Ser Val Asn Gln Pro Val Phe Ser Cys
            35                  40                  45

Ser Ala Asp Trp Gln Arg Ile Ser Asp Phe Asn Ala Lys Ser Gly Cys
        50                  55                  60

Asp Gly Gly Ser Ala Tyr Ser Cys Ala Asp Gln Thr Pro Trp Ala Val
65                  70                  75                  80

Asn Asp Asn Phe Ser Tyr Gly Phe Ala Ala Thr Ala Ile Ala Gly Gly
                85                  90                  95

Ser Glu Ser Ser Trp Cys Cys Ala Cys Tyr Ala Leu Thr Phe Asn Ser
```

```
              100                 105                 110
Gly Pro Val Ala Gly Lys Thr Met Val Val Gln Ser Thr Ser Thr Gly
            115                 120                 125

Gly Asp Leu Gly Ser Asn Gln Phe Asp Leu Ala Ile Pro Gly Gly Gly
            130                 135                 140

Val Gly Ile Phe Asn Gly Cys Ala Ser Gln Phe Gly Gly Leu Pro Gly
145                 150                 155                 160

Ala Gln Tyr Gly Gly Ile Ser Asp Arg Ser Gln Cys Ser Ser Phe Pro
                165                 170                 175

Ala Pro Leu Gln Pro Gly Cys Gln Trp Arg Phe Asp Trp Phe Gln Asn
            180                 185                 190

Ala Asp Asn Pro Thr Phe Thr Phe Gln Arg Val Gln Cys Pro Ser Glu
            195                 200                 205

Leu Thr Ser Arg Thr Gly Cys Lys Arg Asp Asp Ala Ser Tyr Pro
        210                 215                 220

Val Phe Asn Pro Pro Ser Gly Asn Pro Ser Gly Gly Asn Pro Pro Gly
225                 230                 235                 240

Gly Asn Pro Pro Gly Thr Thr Thr Arg Arg Pro Ala Thr Thr Thr
                245                 250                 255

Gly Ser Ser Pro Gly Pro Thr Gln Ser His Tyr Gly Gln Cys Gly Gly
            260                 265                 270

Ile Gly Tyr Ser Gly Pro Thr Val Cys Ala Ser Gly Thr Thr Cys Gln
        275                 280                 285

Val Leu Asn Pro Tyr Tyr Ser Gln Cys Leu
        290                 295
```

<210> SEQ ID NO 13
<211> LENGTH: 297
<212> TYPE: PRT
<213> ORGANISM: Acremonium thermophilum

<400> SEQUENCE: 13

```
Met Arg Ser Ser Pro Phe Leu Arg Ala Ala Leu Ala Ala Ala Leu Pro
1               5                   10                  15

Leu Ser Ala His Ala Leu Asp Gly Lys Ser Thr Arg Tyr Trp Asp Cys
            20                  25                  30

Cys Lys Pro Ser Cys Gly Trp Ala Gly Lys Ala Ser Val Asn Gln Pro
        35                  40                  45

Val Phe Ser Cys Ser Ala Asp Trp Gln Arg Ile Ser Asp Phe Asn Ala
    50                  55                  60

Lys Ser Gly Cys Asp Gly Gly Ser Ala Tyr Ser Cys Ala Asp Gln Thr
65                  70                  75                  80

Pro Trp Ala Val Asn Asp Asn Phe Ser Tyr Gly Phe Ala Ala Thr Ala
                85                  90                  95

Ile Ala Gly Gly Ser Glu Ser Ser Trp Cys Cys Ala Cys Tyr Ala Leu
            100                 105                 110

Thr Phe Asn Ser Gly Pro Val Ala Gly Lys Thr Met Val Val Gln Ser
        115                 120                 125

Thr Ser Thr Gly Gly Asp Leu Gly Ser Asn Gln Phe Asp Leu Ala Ile
    130                 135                 140

Pro Gly Gly Gly Val Gly Ile Phe Asn Gly Cys Ala Ser Gln Phe Gly
145                 150                 155                 160

Gly Leu Pro Gly Ala Gln Tyr Gly Gly Ile Ser Asp Arg Ser Gln Cys
                165                 170                 175
```

```
Ser Ser Phe Pro Ala Pro Leu Gln Pro Gly Cys Gln Trp Arg Phe Asp
            180             185             190

Trp Phe Gln Asn Ala Asp Asn Pro Thr Phe Thr Phe Gln Arg Val Gln
        195             200             205

Cys Pro Ser Glu Leu Thr Ser Arg Thr Gly Cys Lys Arg Asp Asp Asp
    210             215             220

Ala Ser Tyr Pro Val Phe Asn Pro Pro Ser Gly Gly Ser Pro Ser Thr
225             230             235             240

Thr Ser Thr Thr Thr Ser Ser Pro Ser Gly Pro Thr Gly Asn Pro Pro
            245             250             255

Gly Gly Gly Gly Cys Thr Ala Gln Lys Trp Ala Gln Cys Gly Gly Thr
            260             265             270

Gly Phe Thr Gly Cys Thr Thr Cys Val Ser Gly Thr Thr Cys Gln Val
        275             280             285

Gln Asn Gln Trp Tyr Ser Gln Cys Leu
290             295
```